US012740874B2

(12) United States Patent
Babaris et al.

(10) Patent No.: US 12,740,874 B2
(45) Date of Patent: Sep. 22, 2026

(54) BONE MILLING MODULE WITH LOCKING MECHANISM AND RELATED SYSTEMS

(71) Applicant: Stryker Corporation, Kalamazoo, MI (US)

(72) Inventors: Robin B. W. Babaris, Portage, MI (US); Aaron Levi Hoffmann, Plainwell, MI (US); Matthew Glenn Leclercq, Delton, MI (US); Jason James Wroblewski, Portage, MI (US)

(73) Assignee: Stryker Corporation, Portage, MI (US)

( * ) Notice: Subject to any disclaimer, the term of this patent is extended or adjusted under 35 U.S.C. 154(b) by 600 days.

(21) Appl. No.: 17/999,003

(22) PCT Filed: May 24, 2021

(86) PCT No.: PCT/US2021/033859
§ 371 (c)(1),
(2) Date: Nov. 16, 2022

(87) PCT Pub. No.: WO2021/237200
PCT Pub. Date: Nov. 25, 2021

(65) Prior Publication Data

US 2023/0233338 A1 Jul. 27, 2023

Related U.S. Application Data

(60) Provisional application No. 63/028,661, filed on May 22, 2020.

(51) Int. Cl.
*A61F 2/46* (2006.01)

(52) U.S. Cl.
CPC .... *A61F 2/4644* (2013.01); *A61F 2002/4645* (2013.01)

(58) Field of Classification Search
CPC ....................... A61F 2/4644; A61F 2002/4645
See application file for complete search history.

(56) References Cited

U.S. PATENT DOCUMENTS 3,985,304 A 10/1976 Sontheimer
5,970,860 A 10/1999 Yip
(Continued)

FOREIGN PATENT DOCUMENTS

CN 1260244 A 7/2000
CN 110505951 A 11/2019
(Continued)

OTHER PUBLICATIONS

International Search Report for Application No. PCT/US2021/033859 dated Sep. 7, 2021, 4 pages.
(Continued)

*Primary Examiner* — Samuel S Hanna
(74) *Attorney, Agent, or Firm* — Howard & Howard Attorneys PLLC

(57) ABSTRACT

A milling module for converting bone stock into bone chips comprises a shell adapted for removeable attachment to a base module including a motor. The shell comprises a body, a milling element, a lid, and a locking element. The milling element for converting bone stock into bone chips is movably disposed in the shell. The lid is shaped for removeable attachment to the body to allow removal of residual bone chips from the milling element. The locking element is movable between an unlocked position wherein the locking element is positioned relative to the lid to allow removal of the lid from the body, and a locked position wherein the locking element is positioned relative to the lid to prevent removal of the lid from the body.

15 Claims, 19 Drawing Sheets

(56) References Cited

U.S. PATENT DOCUMENTS

| | | | |
|---|---|---|---|
| 6,637,681 | B1 | 10/2003 | Planca et al. |
| 6,681,464 | B1 | 1/2004 | Dupuis et al. |
| 8,002,774 | B2 | 8/2011 | Burmeister, III et al. |
| 8,343,156 | B2 | 1/2013 | Burmeister, III et al. |
| 8,672,942 | B2 | 3/2014 | Chamberlin et al. |
| 8,746,600 | B2 | 6/2014 | Burmeister, III et al. |
| 9,370,436 | B2 | 6/2016 | Stratton |
| 9,655,631 | B2 | 5/2017 | Peterson et al. |
| 9,687,361 | B2 | 6/2017 | Diehl et al. |
| 10,016,204 | B2 | 7/2018 | Burmeister et al. |
| 10,034,673 | B2 | 7/2018 | Lynch et al. |
| 10,045,863 | B2 | 8/2018 | Stratton et al. |
| 10,556,311 | B2 | 2/2020 | Wierzchon et al. |
| 10,588,757 | B2 | 3/2020 | Stratton et al. |
| 10,821,006 | B2 | 11/2020 | Horton, IV et al. |
| 10,828,048 | B2 | 11/2020 | Lynch et al. |
| 10,849,633 | B2 | 12/2020 | Burmeister et al. |
| 11,452,621 | B2 | 9/2022 | Stratton et al. |
| 11,564,813 | B2 | 1/2023 | Babaris et al. |
| 2008/0217446 | A1 | 9/2008 | Clapp et al. |
| 2009/0118735 | A1 * | 5/2009 | Burmeister, III .. A61B 17/1615 606/169 |
| 2013/0062446 | A1 | 3/2013 | Burmeister, III et al. |
| 2014/0076208 | A1 | 3/2014 | Schulz et al. |

FOREIGN PATENT DOCUMENTS

| | | | |
|---|---|---|---|
| DE | 3121252 | A1 | 5/1982 |
| JP | S60109555 | U | 7/1985 |
| TW | 201143188 | A | 12/2011 |
| WO | 2009061728 | A1 | 5/2009 |
| WO | 2011057088 | A1 | 5/2011 |
| WO | 2013102134 | A2 | 7/2013 |
| WO | 2017019827 | A2 | 2/2017 |
| WO | 2018218173 | A9 | 2/2019 |
| WO | 2020139995 | A1 | 7/2020 |

OTHER PUBLICATIONS

Machine-assisted English language abstract for DE 31 21 252 A1 extracted from espacenet.com database on Nov. 20, 2022, 3 pages.
Machine-assisted English language translation for JPS 60-109555 U extracted from espacenet.com database on Jan. 10, 2025, 3 pages.

* cited by examiner 314
340
334
328
320
F2-3
344
342
324
318
313
F1-3
338
326
312

BONE MILLING MODULE WITH LOCKING MECHANISM AND RELATED SYSTEMS

CROSS-REFERENCE TO RELATED APPLICATION

This application is the National Stage of International Application No. PCT/US2021/033859, filed May 24, 2021, which claims priority to and all the benefits of U.S. Provisional Patent Application No. 63/028,661, filed May 22, 2020, the entire contents of which are hereby incorporated by reference.

FIELD OF THE DISCLOSURE

This disclosure relates generally to a milling module for converting bone stock into bone chips that can be used in surgical procedures. More particularly, this disclosure is generally related to a modular system for converting bone stock into bone chips including a base modules and a milling module.

BACKGROUND OF THE DISCLOSURE

Conventional medical and surgical procedures routinely involve the use of bone fragments, often collectively referred to as bone graft, to bridge gaps between bone segments and provide a natural foundation for bone growth.

For example, spinal procedures (e.g. discectomy) utilize bone graft. In such procedures, bone graft is inserted around implanted rods, which hold adjacent vertebrae in alignment. The bone graft serves as a lattice upon which tissues forming the vertebrae grow to form a foundation of bone around the rods. This foundation distributes the load imposed on the rods. In addition, bone graft may also be placed in the intervertebral disc space or into a cage positioned in the intervertebral disc space.

As another example, orthopedic surgical procedures such as joint reconstruction and revision procedures and maxillofacial procedures utilize bone graft. In such procedures, bone graft is used as a filler and/or growth formation lattice in these procedures because the proteins from which the bone is formed serve as make-up material from which the blast cells of the adjacent living bone cells form new bone.

The ideal source of bone stock for bone fragments is the patient into whom the bone fragments are to be packed. This is because the patient's own bone is less likely than donor bone to be rejected by the patient's immune system. Accordingly, in a procedure in which bone chips are required, bone stock is often harvested from one of the patient's bones that may afford to lose a small section of bone, typically between 0.25 and 3 cubic centimeters. Bone stock that is removed from the patient for transplant into another part of the patient is referred to as autograft bone stock.

Converting bone stock into bone fragments is typically a two-part process. In the first part of the process, the harvested bone is prepared for milling and use by removing the ligaments and other soft tissue that is not suitable for forming bone fragments. The prepared bone is then milled into bone fragments, which are used as bone graft. When bone stock is harvested to convert the stock into bone chips, ideally no more bone stock is harvested than is needed to supply the necessary volume of bone chips. This is because minimizing the volume of bone stock that is harvested from the patient results in a like minimization of the trauma to the bone from which the stock was harvested and the tissue that surrounds that bone.

SUMMARY AND ADVANTAGES

A milling module for converting bone stock into bone chips is disclosed. The milling module includes a shell adapted for removable attachment to a base module including a motor. The shell defines includes a body, a milling element, a lid, and a locking element. The milling element for converting bone stock into bone chips is movably disposed in the shell. The lid is shaped for removable attachment to the body to allow removal of residual bone chips from the milling element. The locking element is movable between an unlocked position wherein the locking element is positioned relative to the lid to allow removal of the lid from the body, and a locked position wherein the locking element is positioned relative to the lid to prevent removal of the lid from the body.

A modular system for converting bone stock into bone chips is also disclosed. The modular system includes a base module including a motor, a milling module, and a locking element. The milling module includes a shell adapted for removable attachment to the base module. The shell includes a body, a milling element for converting bone stock into bone chips movably disposed in the shell, and a lid shaped for removable attachment to the body. The locking element has a control surface and a locking portion. Further, the locking element is movable between a locked position in which the lid cannot be removed, and an unlocked position where the lid can be removed. When the milling module is attached to the base module, the control surface is inaccessible for actuation and the locking element is in the locked position, and wherein when the milling module is not attached to the base module, the control surface is accessible for actuation.

A method of converting bone stock into bone chips with the modular system is also disclosed. The method includes the steps of: actuating the milling element to convert bone stock into bone chips while the milling module is attached to the base module; detaching the milling module from the base module so that the control surface on the locking element is accessible; applying force to the control surface to move the locking element into an unlocked position to allow removal of the lid from the body subsequent to detachment of the milling module from the base module; and removing the lid from the body of the shell of the milling module.

A second example of a milling module is disclosed. In this example, the milling module configured for use with a base module including a motor, a controller, and a support surface comprising an alignment tooth, a sensor, and a boss. The milling module includes a shell adapted for removable attachment to the base module. The shell comprises a bottom surface and an exterior wall extending about the periphery of the bottom surface. An alignment guide is shaped in the exterior wall to receive an alignment tooth on the base module, the alignment guide is configured to align the milling module with the base module to facilitate efficient and proper attachment of the milling module to the base module. Further, a module retention element extends from the bottom surface and defines a void to engage the boss on the base module and dissipate rotational energy when the milling module is in use. The bottom surface has a magnet mounted thereon; the magnet is detectable by the sensor when the milling module is attached to the base module. A milling element for converting bone stock into bone chips is movably disposed in the shell.

A second example of a modular system for converting bone stock into bone chips is also disclosed. The modular system includes a base module including a motor, a milling module, and a locking element. The milling module includes a shell adapted for removable attachment to the base module. The shell includes a body, a milling element for converting bone stock into bone chips movably disposed in the shell, and a lid shaped for removable attachment to the body. The locking element is movable between an unlocked position wherein the locking element is positioned relative to the lid to allow removal of the lid from the body, and a locked position wherein the locking element is positioned relative to the lid to prevent removal of the lid from the body.

The milling modules, modular systems, and methods of converting bone stock into bone chips disclosed herein are designed to ensure the largest possible yield of bone chips. Further, the locking element of the milling module is designed to reduce the likelihood that, in the event the milling module is attached to the base module, the lid of the milling module cannot be removed and the milling element internal to the milling module ensures substantial elimination of the possibility of damage or physical harm during removal of residual bone chips from the milling module post milling.

BRIEF DESCRIPTION OF THE DRAWINGS

The disclosure is pointed out with particularity in the claims. The above and further features and benefits of this disclosure are understood from the following Detailed Description taken in conjunction with the accompanying drawings in which:

FIGS. 1-22 are exemplary in nature, are not necessarily drawn to scale, and are thus not intended to represent the relative sizes of the various components of the system described herein.

DETAILED DESCRIPTION

Figure 1:
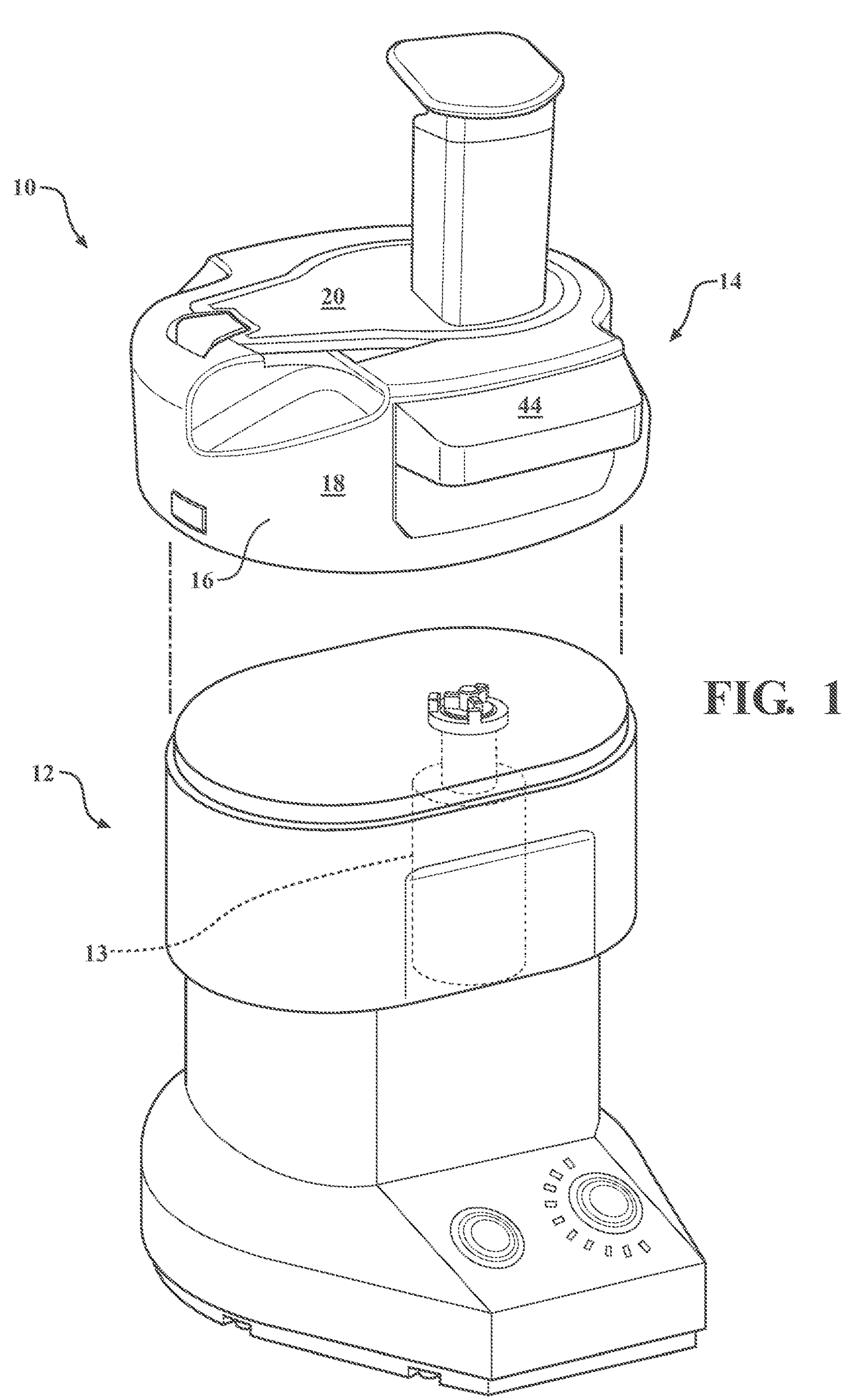
FIG. 1 is an exploded perspective view of an example modular system for converting bone stock into bone chips including a base module and a milling module.

Referring to the Figures, a modular system ("system") 10 for milling bone stock and optionally preparing (e.g. cleaning) bone stock prior to milling is disclosed. An example of the system 10 is illustrated in FIG. 1. The system 10 can also be referred to as a bone mill. The system 10 includes a base module 12. Internal to the base module 12 is a motor 13 and a drive train. The system 10 also includes a milling module 14 for converting bone stock into bone chips, which is removably attachable to the base module 12. The milling module 14 can also be referred to as a mill head. The system 10 may optionally include a preparation module (not illustrated) for cleaning bone, which, like the milling module 14, is also removably attachable to the base module 12. The base module 12 is configured to power the milling module 14 and the preparation module.

FIG. 1 is an exploded perspective view of the system 10 with the milling module 14 detached from the base module 12. In the example illustrated in FIG. 1, the base module 12 is reusable, and the milling module 14 is disposable. As such, the milling module 14 may thus be discarded after use, and a milling module 14 (which is unused or has been cleaned/recycled) may be attached for further use. Of course, other examples of the system 10 include the milling module 14 that is reusable and may be cleaned and/or autoclaved between uses.

The milling module 14 of this disclosure is constructed to ensure that, to the extent possible, the bone chips produced during the milling process are recovered. This ensures that, to the extent possible, for a given volume of bone stock that is milled, the largest possible volume of bone chips is recovered and available for the surgical procedure requiring the use of the bone chips.

The milling module 14 and base module 12 of this disclosure are further designed to reduce the likelihood that, in the event the milling module 14 is attached to the base module 12, a lid 20 of the milling module 14 cannot be removed and a milling element internal to the milling module 14 which is configured to convert bone stock into bone chips cannot be actuated. This ensures substantial elimination of the possibility of damage or physical harm during removal of residual bone chips from the milling module 14 post milling.

Figures 2, 3:
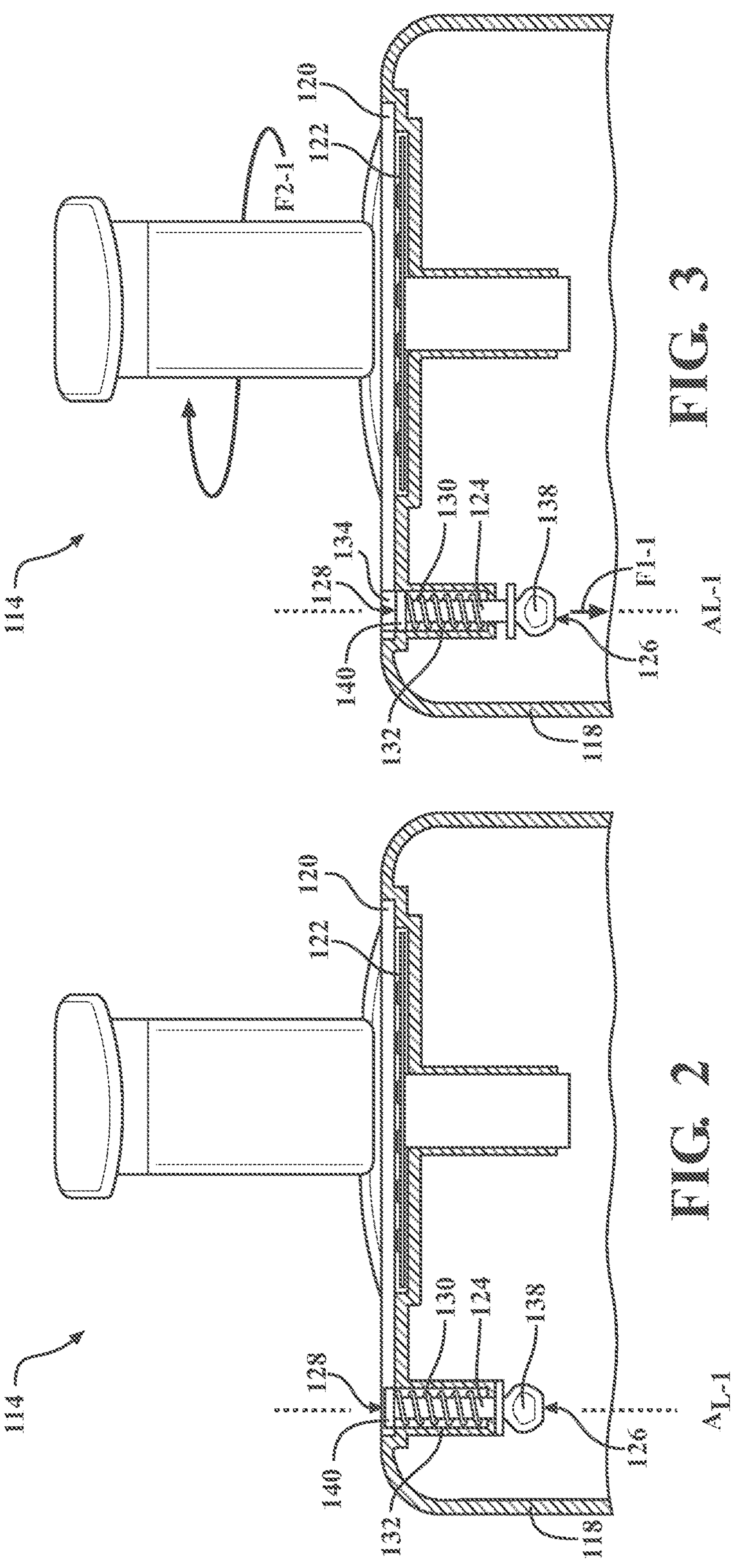
FIG. 2 is a partial, cross sectional view of a milling module including a lid and a locking element in a locked position preventing removal of the lid from the body.
FIG. 3 is a partial, cross sectional view of the milling module of FIG. 2 with the locking element in an unlocked position allowing removal of the lid from the body.

Referring now to FIG. 2, a milling module 114 for converting bone stock into bone chips including a shell 16 adapted for removable attachment to the base module 12 that includes a motor 13 is disclosed. The shell 16 defines an inlet opening through which bone stock is introduced into the shell 16 and an outlet opening through which bone chips are discharged from the shell 16. The shell 16 includes, the body 118, the milling element 122 for converting bone stock into bone chips movably disposed therein, and the lid 120 shaped for removable attachment to the body 118 so that residual bone chips can be removed from the milling element 122, and a locking element 124. The locking element 124 is movably mounted to the body 118 and configured to engage the lid 120 when the shell 16 is removably attached to the base module 12. The locking element 124 is movable between an unlocked position wherein the locking element 124 is positioned relative to (in this example disengaged with) the lid 120 such that the lid 120 can be removed from the body 118, and a locked position wherein the locking element 124 is positioned relative to (in this example engaged with) the lid 120 to prevent removal of the lid 120 from the body 118. The milling element 122 is located below the inlet opening. The milling element 122 converts the bone stock into bone chips.

In one version of the disclosure, the milling element is shaped to push bone stock against an impingement plate. The impingement plate is integral with or secured to the shell 16. As a result of the action of the milling element pushing bone stock against the impingement plate, the bone stock is sheared into bone chips which are smaller in size/volume than the bone stock. Most to the bone chips drop below the milling element. In many versions of the disclosure, the bone chips drop into a catch tray 44. The catch tray 44 is removable from the shell 16.

The milling module 14 of this disclosure is further designed so the shell 16 includes a body 18 to which the lid 20 is removably attached. The removability of the lid 20 makes it possible to access the milling element. Once the lid 20 is removed, the milling element may be removed through the opening in the body 18, which was previously covered by the lid 20 or from the underside of the milling module 14 if the milling module 14 is detached from the base module 12. In many versions of the disclosure, the milling element includes a handle. In many examples disclosed herein the lid 20 of the milling module 14 can only be removed from the body 18 of the shell 16 when the milling module 14 is not attached to the base module 12. Otherwise, when the milling module 14 is attached to the base module 12, the milling module 14 is configured so that the lid 20 is locked in place and cannot be removed from the body 18. Once bone chips are formed, the milling module 14 is removed from the base module 12 and then the lid 20 is removed. Once the lid 20 is removed, the milling element is removed from the shell 16. Using an appropriate tool, such as a scraper, bone chips that adhered to the milling element are scraped off the milling element into the catch tray 44 that holds the bone chips. Further, with the lid 20 off and the milling element in place or removed, bone chips that are adhered to inner surfaces of the body 18 of the milling module 14 can be recovered for use as well. Typically, during this part of the procedure, the person recovering the bone chips that may have otherwise been discarded typically holds the milling element by the handle.

In some examples, the catch tray 44 and the lid 20 are removably attached to the body 18. In these versions of the disclosure, one or both of the lid 20 and the catch tray 44 is provided with a detection component. In these versions of the disclosure, the system 10 is designed so that these components, when in place (appropriately attached to the body 18 of the milling module 14), are detected by a sensor in the base module 12. In turn, if the sensor does not detect the presence of either one or both of the detection components, the system 10 will not operate, e.g. the motor 13 can be actuated. This alerts the individual performing the milling process that there is likelihood that the system 10 is in a state in which the lid 20 is not secured to the body 18 and/or the catch tray 44 is not correctly seated in the body 18 of the shell 16. In one example, the system 10 can be configured such that controller will not allow power to the motor 13 and thus prevents actuation of the milling element when the lid 20 is removed from the body 18.

The shell 16 is further constructed so the inlet opening is formed in the lid 20. In some versions of the disclosure, the shell 16 is further constructed so there is an outlet opening in the body 18 through which the bone chips drop into the catch tray 44. In some examples of this version of the disclosure, the outlet opening is at least partially in line with the inlet opening. In some examples of the disclosure, the shell 16 includes features that facilitate the releasable coupling of the milling module 14 to the base module 12 that drives the milling element. In these examples of the disclosure, the milling element is formed with features that releasably couple the milling element to a drive spindle that actuates the milling element. Often these milling element drive features that releasably couple the milling element to the drive spindle are accessible through a specific opening in the shell 16 that is present in part for that very purpose. In some versions of the disclosure, the milling element is configured to rotate in the shell 16. In some examples of this version of the disclosure, a shaft transfers the rotational movement of the drive spindle to the milling element so as to rotate the milling element. In these examples of the disclosure, the shaft is bi-functional. In addition to serving as a drive-link, the shaft functions as the handle that is held when the bone chips that have adhered to the milling element are being recovered. The base module 12 includes a base shell. The base shell houses many components of the base module 12. The base shell has a top surface. Internal to the base shell is the motor 13. Also internal to the base shell is a drive spindle. The drive spindle has a head that extends through an opening in the top surface of the base shell. The motor 13 drives the drive spindle. When the milling module 14 is attached to the base module 12, the drive spindle engages the milling element. The rotation of the drive spindle results in a like rotation of the milling element. The base module 12 may include plural tabs (two tabs are illustrated in FIG. 1). The tabs can be movably mounted to and extend outwardly from the base shell. A linkage assembly may be configured to move the tabs into and out of plural openings on the body 18 of the milling module 14. The milling module 14 is positioned on or fitted over the top surface of the base module 12, and the linkage assembly can be used to engage or disengage the plural tabs with the plural openings. When the tabs are engaged in the openings, the base module 12 releasably holds the milling module 14 static thereto. When the tabs are disengaged from the openings, the milling module 14 can be released from the base module 12. It should be appreciated that various mechanisms known to those in the mechanical arts may be utilized to removably attach (i.e. releasably couple) the milling module 14 to the base module 12.

Also shown as mounted to the base shell is a control button. The control button is part of a control circuit. The control circuit may also include the sensor disposed in the base shell below the top surface. The sensor is configured to detect an indicator. In one example, the sensor is a hall-effect sensor. The state of the control button as well as the signal output by the sensor are applied to a controller also disposed in the base shell. The controller is connected to both a power supply and the motor 13. The controller is configured to regulate the application of current to the motor 13 to actuate the motor 13. In many constructions of system 10, the controller is configured to only actuate the motor 13 during time periods in which the button is depressed.

The Applicant's Patent Cooperation Treaty ("PCT") application nos. PCT/US2008/082348 (WO2009061728), PCT/US2010/055646 (WO2011057088), PCT/US2012/072160 (WO2013102134), PCT/US2016/044386 (WO2017019827), PCT/US2018/034700 (WO2018218173), and PCT/US2019/068660 (WO2020139995), the contents of each of which are hereby incorporated by reference, disclose electrically operated systems for converting bone stock into bone chips including milling modules, preparation modules, and base modules. The milling module 14, as seen in FIG. 1, includes the body 18 to which the lid 20 is removably attached. Collectively, the body 18 and the lid 20 form the shell 16 of the milling module 14. The shell 16 is adapted for releasable attachment to the base module 12. The shell 16 includes the inlet opening through which bone stock is introduced into the milling module 14 and the outlet opening through which bone chips are discharged from the milling module 14. The milling element is moveably disposed in the shell 16 between the inlet opening and the outlet opening for converting bone stock into bone chips. The milling element includes features for removably attaching the milling element to the motor 13 so that the actuation of the motor 13 results in the actuation of the milling element. The body 18 of the milling module 14 is adapted for releasable attachment to the base module 12. The body 18, as seen in FIG. 1, may include a rim. The rim is dimensioned to seat around an outer perimeter of the top surface of the base module 12. The rim is formed with the plural openings. The body 18 is formed so that when the milling module 14 is seated over the base module 12 top surface, each of the plural tabs integral with the base module 12 can seat in and extend through each of the plural openings in the rim to attach and secure the milling module 14 to the base module 12. That is, the body 18 includes the rim having plural openings and is dimensioned to seat around the outer perimeter of the top surface of base module 12, when seated the plural tabs on the base module 12 extend through the plural openings to become integral with the plural openings and attach the milling module 14 to the base module 12.

The body 18 of the milling module 14 may have a recessed surface that may be generally circular in shape. The recessed surface includes one (or in some examples two) openings. A first opening is concentric with the center of the recessed surface, circular in shape, and configured to receive the head of the drive spindle. If a second opening is included, it can be first a perimeter of the recessed surface, circular in shape, and configured to receive rotational energy to actuate various internal features that may be included in the milling module 14 or the cleaning module. The body 18 of the milling module 14 also includes the outlet opening. The outlet opening, extends inwardly from a sidewall of the body 18. The body 18 may be formed with two steps extending radially about an opening in a top panel of the body 18. The body 18 is further formed so as to have plural notches that extend inwardly from the perimeter of the top panel that defines the opening. In some examples, the body 18 is further formed to have a tube-like sleeve that extends downwardly from the recessed panel. More particularly, the sleeve extends downwardly from the recessed panel so as to extend around the portion of the panel that defines the perimeter of an opening. The system 10 is designed so that when the milling module 14 is attached to the base module 12, the opening and the sleeve are coaxial with the drive spindle.

The body 18 also includes the lid 20. The lid 20 is removably attached to the body 18. The lid 20 includes the inlet opening of the shell 16. The body 18 and the lid 20 are collectively configured so that removal of the lid 20 from the body 18 allows the milling element to be accessed. As is described in detail below, the milling element is removably attached to the body 18 of the shell 16.

The lid 20 is shaped to have a disc-shaped foundation that defines an inner surface. In some examples, the foundation is domed. The foundation of the lid 20 is shaped to fit in the opening. More particularly, an outer perimeter of the foundation of the lid 20 is dimensioned to seat on the step. The foundation includes one or more tabs that project radially outwardly from a cylindrical side wall of the foundation. The one or more tabs are positioned and dimensioned so that when the foundation of the lid 20 is positioned in an opening in the body 18 and rotated, each tab rotates into a respective notch in the body 18 to become integral with the notch and attaches the lid 20 to the body 18. For example, in some examples, three tabs project radially outwardly from the cylindrical side wall of the foundation. The tabs are positioned and dimensioned so that when the foundation is seated in the opening, each tab seats in and is able to rotate in a separate one of the notches. That is, the components forming the system 10 are shaped so that the foundation can rotate into the opening, and so that when the lid 20 is rotated, the tabs are able to rotate into the notches and become integral with the notches. The foundation includes one or more rings which extend downwardly from the inner surface of the foundation. One of the one or more rings is concentric with the foundation, positioned on an outer perimeter of the foundation, and seats against the step on the body 18 when fitted thereto. The foundation is also shaped to have the inlet opening. The foundation is formed so that when the lid 20 is attached to the body 18, the inlet opening is in line with and located above the opening.

Lid 20 also includes a feed sleeve. The feed sleeve extends upwardly from the outer surface of the foundation of the lid 20 and surrounds the inlet opening. An impingement plate (not illustrated) is rigidly mounted to the lid 20. The components forming the milling module 14 are constructed so that the impingement plate has a surface that is located immediately below the perimeter of the inlet opening in the foundation of the lid 20. The milling element of the milling module 14, includes a circularly shaped planar cutting disc. Other shapes of the milling element are also contemplated, i.e., non-circular shapes. Located around the center of the cutting disc are four equiangularly shaped apart openings. The cutting disc includes features that convert bone stock into bone chips. That is, the cutting disc is further formed to have a number of cutting scallops. Integral with and longitudinally axially aligned with each cutting scallop, the cutting disc has a through opening. More particularly, the cutting disc is formed so that each cutting scallop extends above the planar top surface of the milling element. The scallops are milled to define cutting edges. Each cutting edge partially defines the parameter of the adjacent opening. A shaft, also part of the milling element, extends downwardly from the center of the cutting disc. In a typical example, the shaft is permanently attached to the cutting disc. The shaft is configured to connect to the cutting disc and the drive spindle and remains attached to the cutting disc during removal of the milling element from the body 18 and is adapted to be held. As such, the shaft extends from the cutting disc and is formed with the features that removably couple the milling element to the motor 13 of the base module 12.

The shaft is generally cylindrical in shape. The shaft is formed to have a head. The shaft head has a diameter that allows the head to seat in and rotate in the sleeve integral with the body 18. A cylindrical stem extends below the head. The stem has a diameter less than that of the head. The bottom end of the stem faces the drive spindle and is formed with a feature for releasably engaging the spindle. In one example, the stem includes one or more notches that extend upwardly from a bottom face of the stem and are spaced radially outwardly from the center of the stem, wherein the one or more notches are configured to engage one or more complementary teeth on a face of the drive spindle of the base module 12 so that the rotation of the drive spindle results in the like rotation of the milling element.

A plunger, seen throughout the Figures, may be slidably mounted in the feed sleeve of the lid 20. The plunger is formed to have a head and a top plate from which a rod extends. The rod is dimensioned to slidably fit in the feed sleeve. The top plate is dimensioned to subtend an area larger than the cross-sectional area of the center void of the feed sleeve. The top plate thus limits the extent to which the plunger rod can be pushed into the feed sleeve and the inlet opening.

The catch tray 44 is slidably disposed in the opening formed in the body 18 of the milling module 14. That is, the catch tray 44 is removably mounted adjacent the outlet opening to receive bone chips discharged therethrough.

In many examples, the shell 16 includes a locking element. The locking element is movably mounted to the body 18 and configured to engage the lid 20, when the shell 16 is removably attached to the base module 12. The locking element is movable between a locked position wherein the locking element is positioned relative to the lid 20 such that the lid 20 cannot be removed from the body 18, and an unlocked position wherein the locking element is positioned relative to the lid 20 such that the lid 20 can be removed from the body 18.

The locking element has a first end and a second end opposite the first end and defines a longitudinal axis. The locking element may include a locking shaft 124, 224, 324 as is illustrated in FIGS. 2-5 or a locking arm 424 as is illustrated in FIG. 6. The locking shaft 124, 224, 324 can have various cross-sectional profiles including, but not limited to, cross-sectional profiles selected from ovular (e.g. round), triangular, and rectangular (e.g. square). The locking element may be coupled to a biasing element, e.g. a spring. In some examples, the biasing element is configured to urge the locking element, e.g. locking shaft, in a first direction along the longitudinal axis of the locking element (e.g. towards the base module 12). In other examples, the biasing element is configured to urge the locking element, e.g. locking shaft, in a second direction along the longitudinal axis of the locking element (e.g. away from the base module 12). In some such examples, the biasing element is adjacent the locking element while in other such examples the biasing element is disposed about an outer circumference of the locking element. The locking element may include a biasing surface that cooperates with the biasing element and the body to bias the locking element in the first or second direction along the longitudinal axis of the locking element. In some examples, the biasing surface is located at the first end of the locking element. In other examples, the biasing surface is located at the second end of the locking element.

Further, the body 18 defines a chamber and the locking element is movably disposed in the chamber. In some examples, the chamber is defined by a locking sleeve and the locking element and the biasing element are disposed in the chamber of the locking sleeve. In some examples, the locking element and the biasing element are disposed within the locking sleeve, and the biasing element is located adjacent the locking element within the locking sleeve. For example, the biasing element can be positioned adjacent the locking element and parallel thereto. In some such examples, the biasing element cooperates with a biasing surface at the first end of the locking element to bias the locking element away from the lid along the longitudinal axis defined by the locking element.

Further, the locking element cooperates with the lid 20 to lock the lid 20 in place when the milling module 14 is attached to the base module 12. In some examples, the lid 20 defines a locking recess. In some examples, the lid 20 includes a locking tab. In some such examples, the locking tab defines the locking recess and the locking element is engaged in the locking recess in the locked position. In other examples, the locking element in the locked position engages with the tab (e.g. a side of the locking tab) to prevent the rotation and removal of the lid 20.

Nonetheless, the lid 20 defines the locking recess and the locking element is movable between the unlocked position and the locked position. In the unlocked position, the locking element is not received within the locking recess in the lid 20 and the lid 20 can be removed (e.g. via rotation) from the body 18. In the locked position, the locking element is received within the locking recess in the lid 20 and the locking element prevents removal (prevents rotation) of the lid 20 from the body 18.

In examples where the chamber is defined by the locking sleeve, and the locking element is disposed in the locking sleeve, the biasing element may be configured to urge the first end of the locking element longitudinally past a first end of the locking sleeve. Still further, in some examples the shell 16 may define a lower plane opposite the lid 20 and the biasing element may even be configured to urge the first end of the locking element longitudinally past the lower plane of the shell 16. In such an example, when the milling module 14 is not attached to the base module 12, the biasing element is configured to urge the locking element into the unlocked position such that the lid 20 can be removed from the body 18. When the milling module 14 is attached to the base module 12, the base module 12 forces the locking element into the locked position to prevent removal of the lid 20 from the body 18. This example, and other examples where the base module is shaped to force the locking element into the locking recess can be referred to as a passive locking configuration because the attachment of the milling module 14 to the base module 12 forces the locking element into the locked position to prevent removal of the lid 20 from the body 18, and once the milling module 14 is removed, the lid 20 automatically reverts to an unlocked position.

In other examples, the locking element includes a tab, and a force can be exerted on the tab to remove the locking element from the locking recess. For example, referring now to FIGS. 2 and 3, the locking element 124 includes the tab 138, and once the milling module 114 is removed from the base module 12, a downward force can be applied to the tab 138 to move the locking element 124 out of the locking recess 134 so that the lid 120 can be removed from the milling module 114. Alternatively, referring now to FIGS. 4 and 5, the locking element 224 includes the tab 238, and once the milling module 214 is removed from the base module 12, an upward force can be applied to the tab 238 to move the locking element 224 out of the locking recess 234 so that the lid 220 can be removed from the milling module 214. These examples can be referred to as having an active locking configuration because the milling module 214 must first be detached from the base module 12, and then a force must be applied to the locking element 224 to move the locking element out 224 of the locking recess 234 and into the unlocked position to allow removal of the lid 220 from the body 218. In these active locking configurations, the locking element 124, 224 is biased into the locking recess 134, 234, and even when removed from the base module 12 a force must be applied to the tab 138, 238 to allow removal of the lid 120, 220. Once the lid 120, 220 is removed from the body 118, 218, the milling element 122, 222 can be accessed or removed from the shell 16 to harvest bone chips that adhered to the milling element 122, 222.

Referring now to FIGS. 2 and 3, the milling module 114 for converting bone stock into bone chips includes the locking element 124 (locking shaft) and the biasing element 130. The biasing element 130 is configured to urge the locking element in a second direction along the longitudinal axis $A_{L-1}$ of the locking element 124. In this example, the biasing element 130 is disposed about an outer circumference of the locking element 124. The body 118 includes the sleeve 132 that defines the chamber that the locking element 124 and the biasing element 130 are moveably disposed in the sleeve 132. In this example, the locking element 124 includes the tab 138 located at the first end 126 of the locking element 124 and a foot 140 at the second end 128 that is configured to be received within the locking recess 134 of the lid 120. A force can be exerted on the tab 138 (the tab 138 can be pulled down in a first direction) to remove the foot 140 from the locking recess 134 and move the locking element 124 from the locked position to the unlocked position to allow subsequent removal of the lid 120 from the body 118. FIG. 2 illustrates the locking element 124 in the locked position. That is, the foot 140 of the locking element 124 is received within the locking recess 134 in the lid 120 and the locking element 124 prevents the rotation and removal of the lid 120 from the body 118. FIG. 3 illustrates the locking element 124 in an unlocked position. That is, the foot 140 of the locking element 124 is not received within the locking recess 134 in the lid 120 as the tab 138 is pulled down $F_{1-1}$ and the lid 120 can be rotationally removed $F_{2-1}$ from the body 118.

Figures 4, 5:
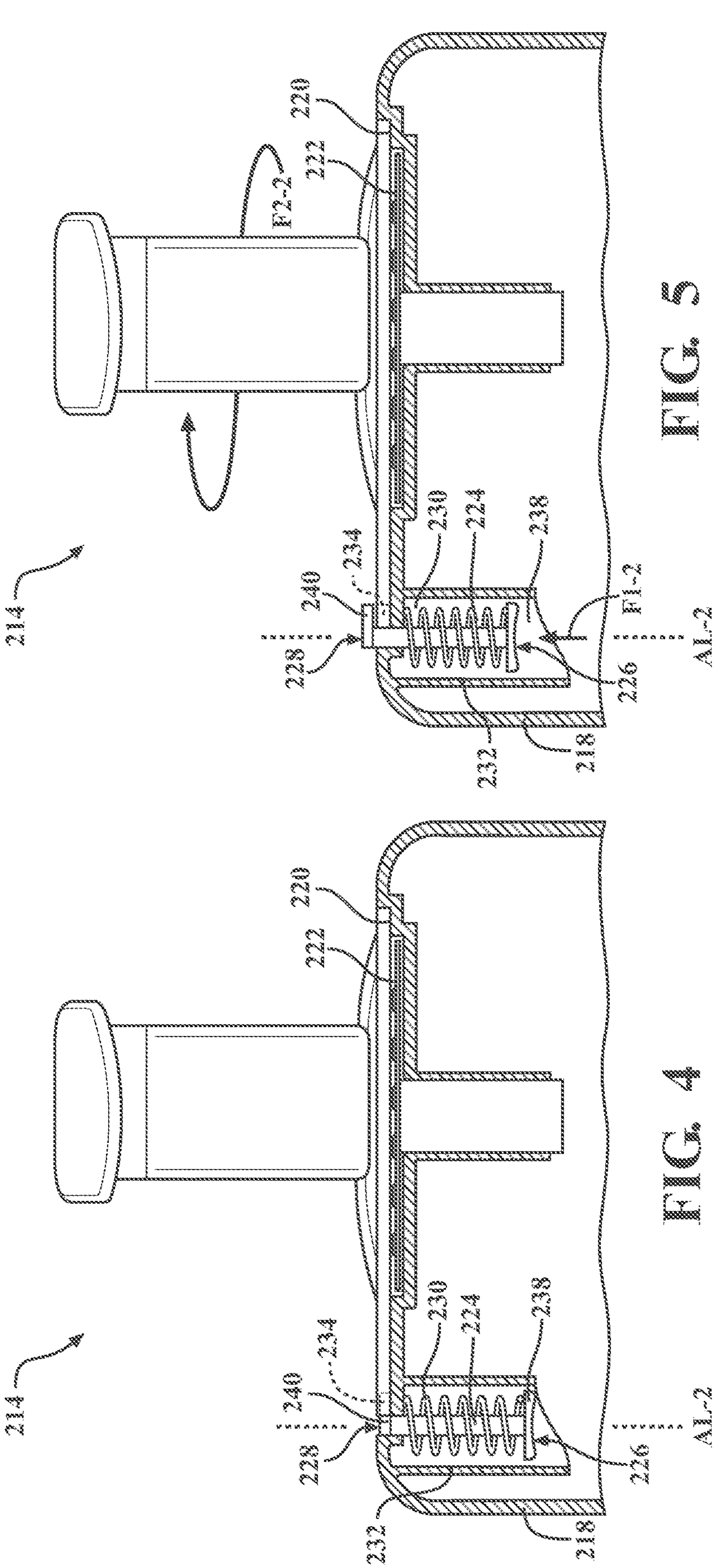
FIG. 4 is a partial, cross sectional view of another milling module including a lid and a locking element in a locked position preventing removal of the lid from the body.
FIG. 5 is a partial, cross sectional view of the milling module of FIG. 4 with the locking element in an unlocked position allowing removal of the lid from the body.
Figure 6:
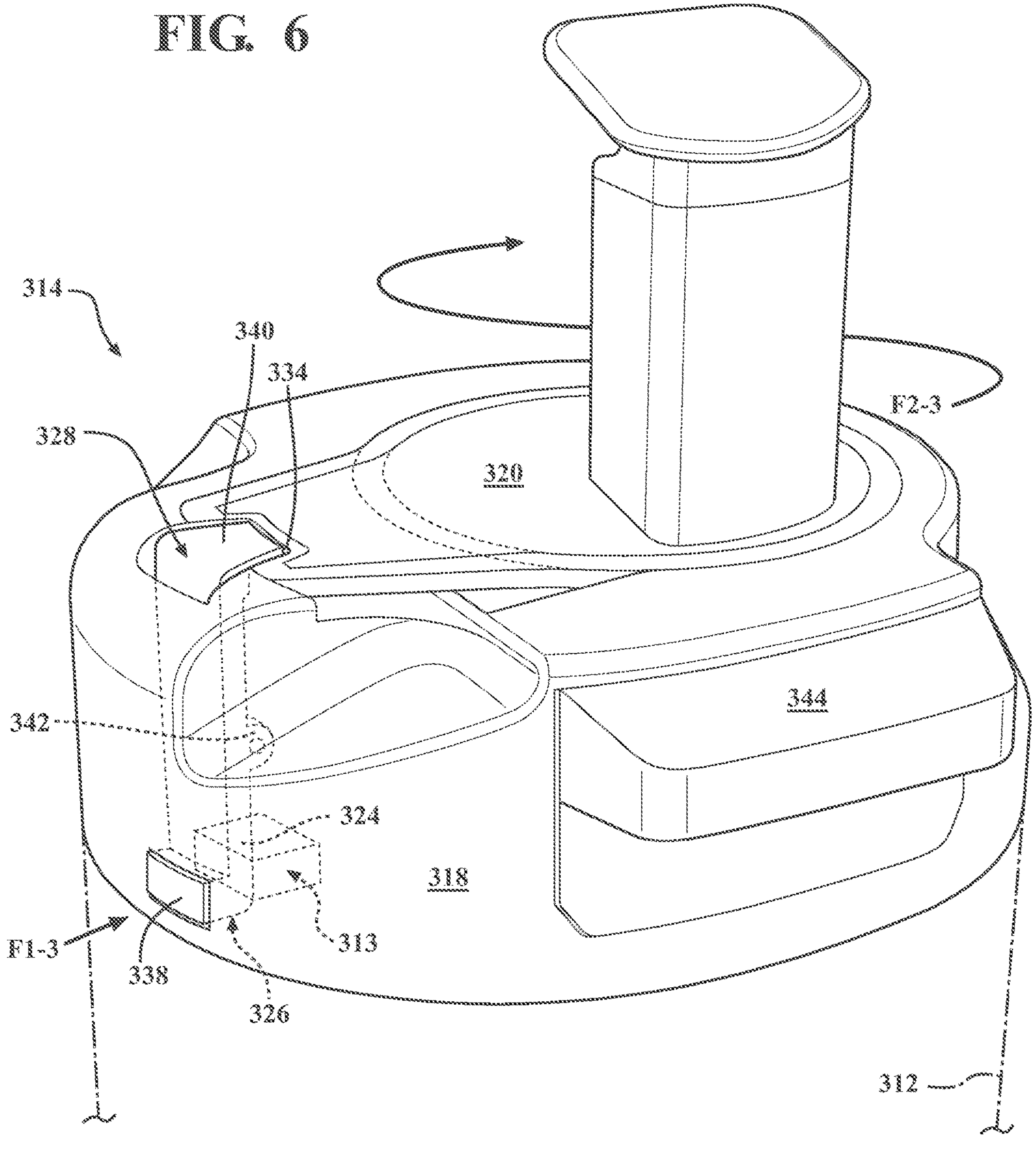
FIG. 6 is a perspective view of a milling module including a lid and locking element including a locking arm that prevents removal of the lid from the body in a locked position.

Referring now to FIGS. 4 and 5, the milling module 214 for converting bone stock into bone chips includes the locking element 224 (locking shaft) and the biasing element 230 which is configured to urge the locking element 224 in a first direction along the longitudinal axis $A_{L-2}$ of the locking element 224. In this example, the biasing element 230 is disposed about an outer circumference of the locking element 224. The body 218 includes the locking sleeve 232 that defines the chamber. The locking element 224 and the biasing element 230 are moveably disposed in the locking sleeve 232. In this example, the locking element 224 includes the tab 238 located at the first end 226 of the locking element 224 and the foot 240 at the second end 228 that is configured to be received within the locking recess 234 in the lid 220, wherein a force (e.g. a push) can be exerted on the tab 238 to remove the foot 240 from the locking recess 234 and move the locking element 224 from the locked position to the unlocked position to allow subsequent removal of the lid 220 from the body 218. FIG. 4 illustrates the locking element 224 in the locked position. The locking recess 234 in this example includes a channel portion in which the locking element 224 (locking shaft) is disposed as well as a recess portion on a top surface of the lid 220. When the tab 238 is pushed, the locking element 224 moves along the longitudinal axis $A_{L-2}$ within the channel portion in a second direction and the foot 240 on the second end 228 of the locking element 224 lifts out of the recess portion in the lid 220 to allow the rotation and removal of the lid 220. That is, the foot 240 of the locking element 224 is received within the locking recess 234 in the lid 220 and the locking element 224 prevents removal of the lid 220 from the body 218. FIG. 5 illustrates the locking element 224 in an unlocked position. That is, the foot 240 of the locking element 224 is not received within the locking recess 234 in the lid 220 as the tab 238 is pulled down $F_{1-2}$ and the lid 220 can be rotationally removed $F_{2-2}$ from the body 218.

Referring now to FIG. 6, the milling module 314 for converting bone stock into bone chips includes the body 318, the lid 320, the catch tray 344, and also the locking element 324. The locking element 324 (a locking arm illustrated in phantom lines) has the first end 326 and the second end 328 and is pivotably mounted to the body 318. In this example, the lid 320 defines the locking recess 334. Further, the locking element 324 includes the foot 340 at the second end 328 which is configured to be received by the locking recess 334 in the lid 320, a mounting element 342, and optionally the biasing element. In some examples, the locking element 324 is biased into the locking recess 334 with the biasing element. In other examples, the foot 340 and the locking recess 334 have an interference-type fit. The mounting element 342 engages the body 318 and the locking element 324 and acts as a pivot point. In some examples, the biasing element can be positioned adjacent the mounting element 342. The locking element 324 is biased into the locked position and exertion of a force $F_{1-3}$ on the first end 326 of the locking element 324 pivots the locking element 324 from the locked position to the unlocked position to allow application of force $F_{2-3}$ and rotation of the lid 320 to remove the lid 320 from the body 318. When the milling module 314 is attached to the base module 312, an abutment element 313 (illustrated in phantom lines abutting those of the locking element 324) on the base module 312 prevents pivoting of the locking element 324 into the unlocked position and subsequent removal of the lid 320 from the body 318. Once the milling module 314 is removed from the base module 312, a force $F_{1-3}$ can be applied to the tab 338 at the first end 326 of the locking element 324 opposite the foot 340, so that the foot 340 is not received within the locking recess 334 in the lid 320, and the lid 320 can be rotationally removed from the body 318 via force $F_{2-3}$.

The milling module 314 of FIG. 6 has an active locking configuration because the milling module 314 must first be detached from the base module 312, and then a force $F_{2-3}$ must be applied to the locking element 324 to move the locking element out 324 of the locking recess 334 and into the unlocked position to allow removal of the lid 320 from the body 318. In this active locking configuration, the locking element 324 is biased into the locking recess 334 and even when removed from the base module 312 a force must be applied to the tab 338 to allow removal of the lid 320. Although the example milling module 314 has an active locking configuration, it should be appreciated that this milling module can be configured to have a passive locking mechanism by utilization of a biasing element that biases the second end 328 of the locking element 324 out of the locking recess 334.

The example milling modules 114, 214, 314 of FIGS. 2-6 and 13-21 as described herein include the lid 120, 220, 320, 820 which defines the inner surface, the outer surface, the side wall, and the one or more tabs that project radially outwardly from the side wall, wherein the one or more tabs are positioned and dimensioned so that when the lid 120, 220, 320, 820 is positioned on the body 118, 218, 318, 818 and rotated, each of the tabs rotate into a respective notch in the body 118, 218, 318, 818 to attach the lid 120, 220, 320, 820 to the body 118, 218, 318. These examples prevent rotation of the lid 120, 220, 320, 820 under certain conditions, which prevents removal of the lid 120, 220, 320, 820 from the body 118, 218, 318, 818.

Figure 7:
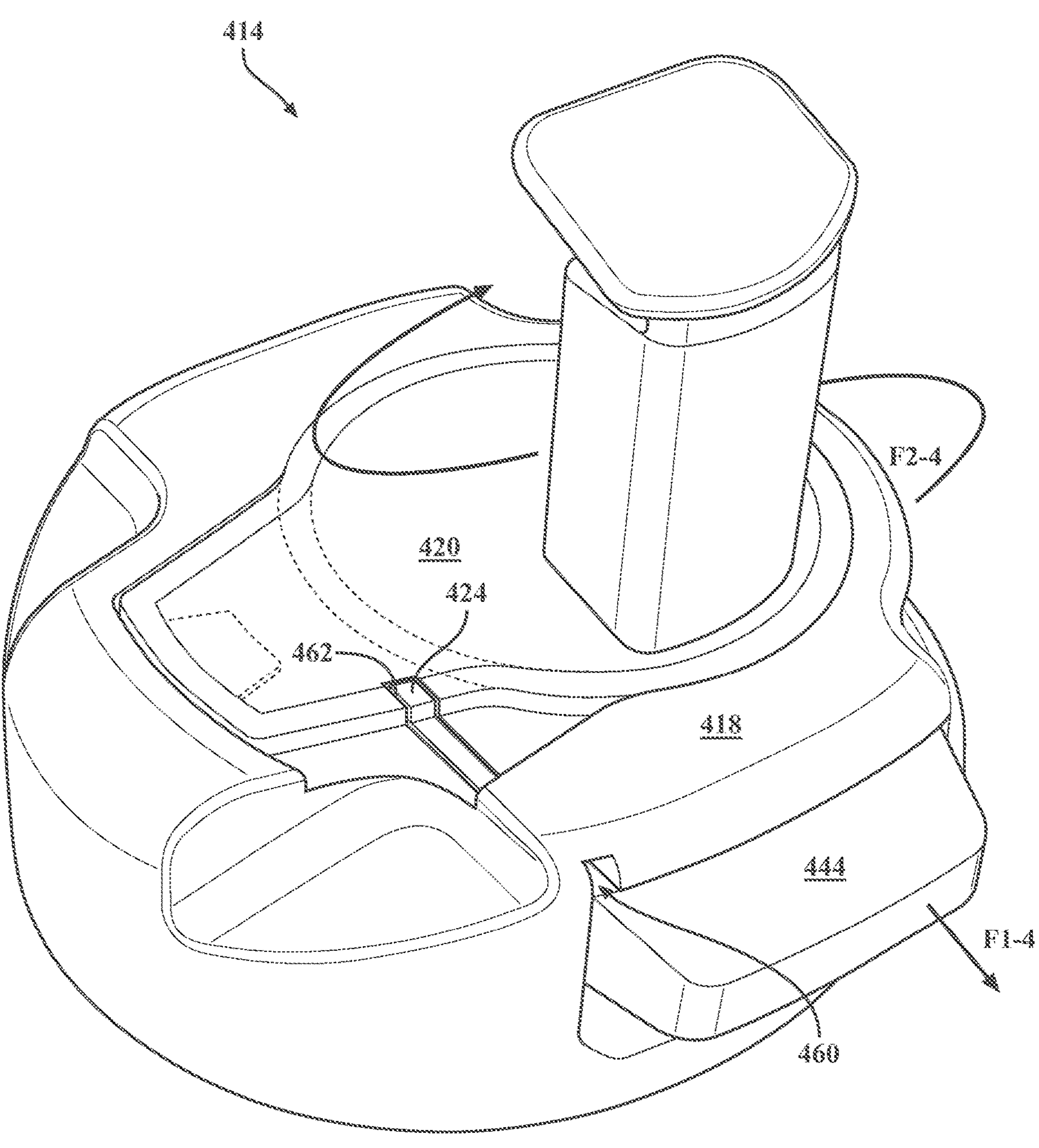
FIG. 7 is a perspective view of yet another milling module including a catch tray with a tab configured to prevent removal of the lid when the catch tray is in place and the milling module is attached to the base module.
Figure 8:
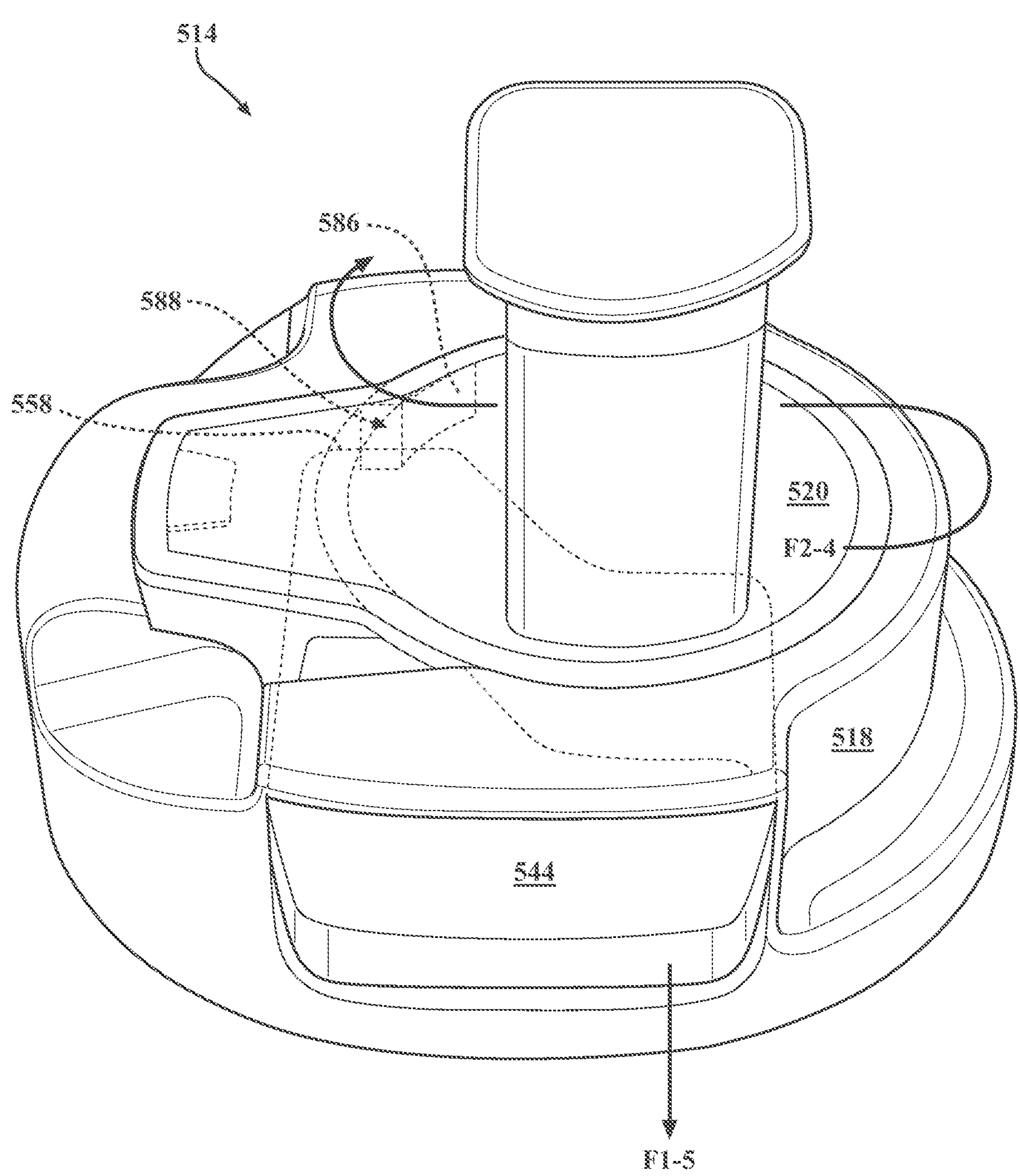
FIG. 8 is a perspective view of yet another milling module including a lid with a retainer that cooperates with a catch tray to prevent removal of the lid when the catch tray is in place and the milling module is attached to the base module.

Referring now to the milling modules 414, 514 of FIGS. 7 and 8, the catch tray 444, 544 is designed to prevent the rotational removal of the lid 420, 520. These particular milling modules 414, 514 are different than those of FIGS. 2-6 in that the catch tray 444, 544 prevents the lid 420, 520 from moving when it is inserted in the milling module 414, 514. That is, if the catch tray 444, 544 is mounted and in place, the lid 420, 520 cannot be removed. Further, the milling modules 414, 514 of FIGS. 7 and 8 utilize a detection system to ensure that the catch tray 444, 544 is properly mounted and in place in the milling module 414, 514. If the catch tray 444, 544 is properly in place in the milling module 414, 514, the detection system cooperates with the controller to allow actuation of the motor 13 and in-turn the actuation of the milling element. If the catch tray 444, 544 is not properly in place in the milling module 414, 514, the detection system cooperates with the controller to prevent actuation of the motor 13 and milling element. As such, the motor 13 can only be actuated if the catch tray 444, 544 is properly in place within the milling module 414, 514, and if the catch tray is properly in place, the lid 420, 520 cannot be removed from the body 418, 518 of the shell to access the milling element. These milling modules 414, 514 will not allow removal of the lid 420, 520 in order to prevent a user from being able to actuate the milling element with the lid 420, 520 off of the milling module 414, 514.

The system of FIGS. 7 and 8 utilizes a sensor attached to the base module 12; the sensor is adapted to monitor the shell for the presence/absence of the catch tray 444, 544 and generate a sensor signal that varies as a function of the presence/absence of the catch tray 444, 544. The controller in the base module 12 is configured to regulate the actuation of the drive assembly based on the sensor signal. When the sensor signal indicates that the catch tray 444, 544 is absent, the controller inhibits actuation of the milling element. In some non-limiting examples, the sensor (e.g. a hall-effect sensor) in the base module 12 is configured to monitor the presence of a magnetic field and a magnet is mounted to the catch tray 444, 544. When the catch tray 444, 544 is properly mounted in the body 418, 518 of the shell and the body 418, 518 is seated in the base module 12, the magnet is located above the sensor. In other examples, other signal generators and sensors known in the art are utilized. In some examples, when the catch tray 444, 544 is properly mounted in the milling module 414, 514, the controller activates a light emitting diode (LED) proximal to the switch to provide a visual indication that the catch tray 444, 544 is mounted in the base module 12.

Referring now to the milling module 414 of FIG. 7, the catch tray 444 includes a base from which panels extend upwardly. The locking element 424 in the form of a tab, is positioned on one or a combination of the panels (illustrated on a side panel in FIG. 7) and extends upwardly therefrom. A channel 460 in the body 418 accommodates the locking element 424 to allow insertion and mounting of the catch tray 444 in the base module 12. When the catch tray 444 is mounted in the milling module 414, it cooperates with a slot 462 on the lid 420 to prevent rotation and removal thereof. That is, the locking element 424 of the catch tray 444 is received within the slot 462 in the lid 420, and the locking element 424 prevents removal of the lid 420 from the body 418. However, referring again to FIG. 7, if catch tray 444 is removed from the milling module 414 via a force $F_{1-4}$ so that the locking element 424 is not received within the slot 462 in the lid 420, and the lid 420 can be rotationally removed from the body 418 via force $F_{2-4}$, and an interior of the milling module 414 can be accessed, but the motor cannot be actuated. As such, the catch tray 444 must be properly mounted in the milling module 414 in order to actuate the motor 13, and if the catch tray 444 is mounted in the milling module 414, the locking element 424 prohibits the rotation and the removal of the lid 420 and subsequent access to the milling element and the interior of the milling module 414.

Referring now to FIG. 8, the lid 520 includes a retainer 586 with a stop surface 588 (illustrated in phantom lines). When the lid 520 is attached to the milling module 514 and the catch tray 544 is mounted in the milling module 514, the stop surface 588 is configured to cooperate with the back surface on the back panel 558 of the catch tray 544 to prevent rotation and removal of the lid 520 from the milling module 514. If the catch tray 544 is properly in place in the milling module 514, the detection system cooperates with the controller to allow actuation of the motor 13 and milling element while removal of the lid 520 from the body 518 is prevented (since rotation of the lid 520 is prevented). Otherwise, if the catch tray 544 is not properly in place the lid 520 can be removed from the body 518, but the detection system cooperates with the controller to prevent actuation of the motor 13 and milling element. That is, if catch tray 544 is removed from the milling module 514 via a force $F_{1-5}$ so that the back surface on the back panel 558 of the catch tray 544 is not positioned to contact the stop surface 588 to prevent rotation of the lid 520, the lid 520 can be rotationally removed from the body 518 via force $F_{2-5}$ and an interior of the milling module 514 can be accessed, but the motor cannot be actuated. As such, the motor 13 can only be actuated if the catch tray 544 is properly in place within the milling module 514, and if the catch tray is properly in place, the lid 520 cannot be removed to access the milling element.

Figure 9:
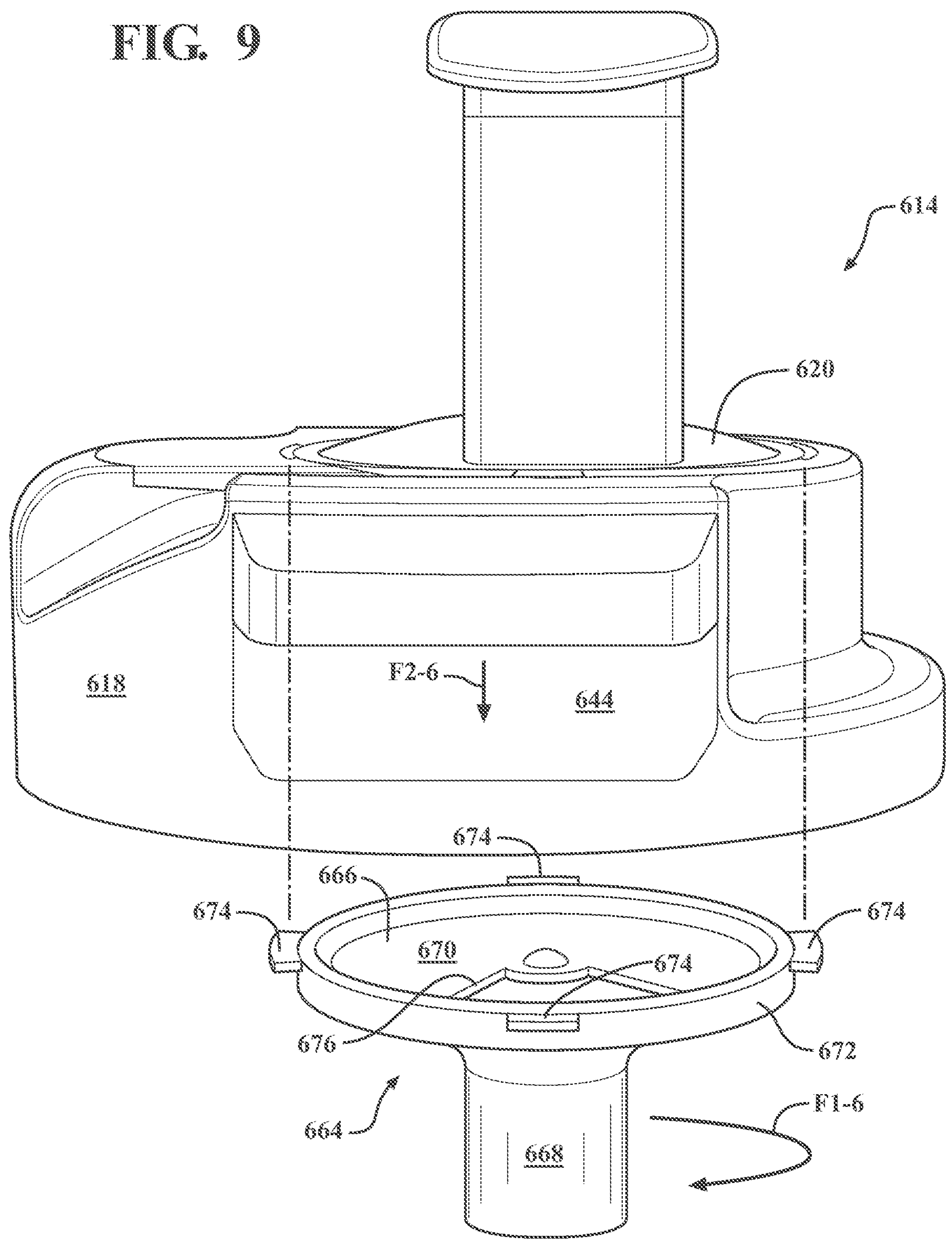
FIG. 9 is a side view of yet another milling module including a removably attached blade retainer.
Figure 10:
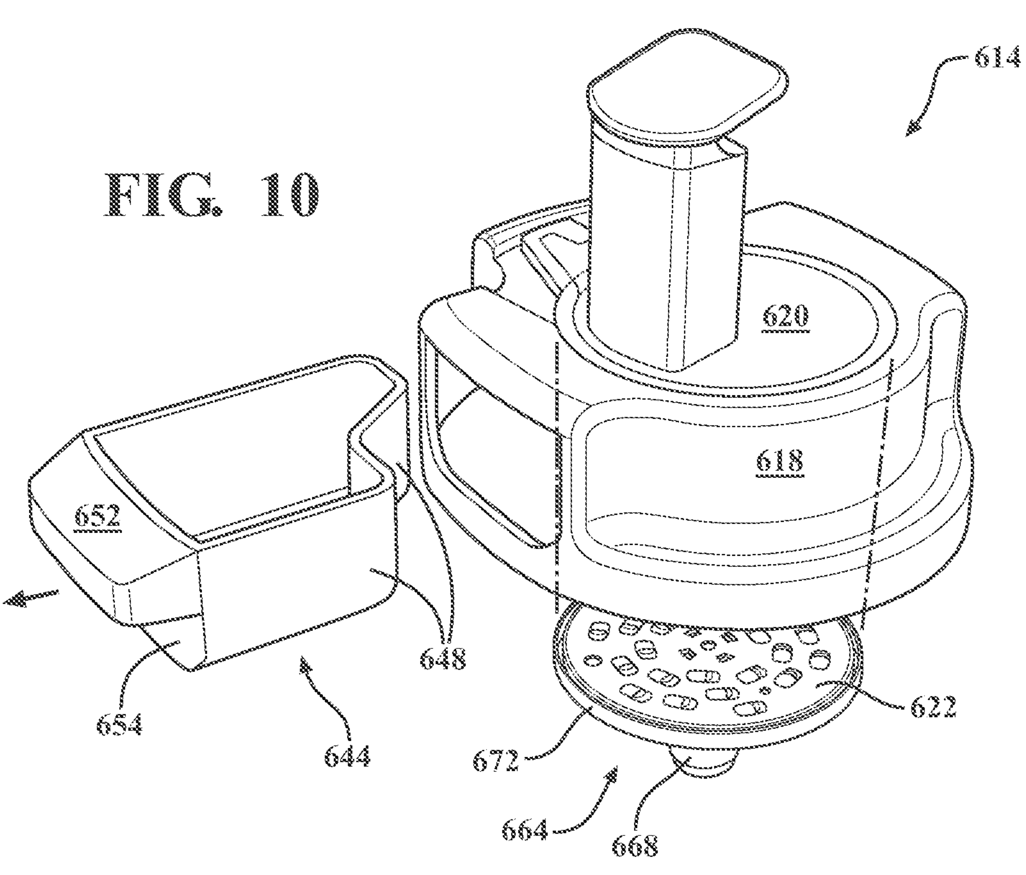
FIG. 10 is a perspective view of the milling module of FIG. 9 having a catch tray removed therefrom.
Figure 11:
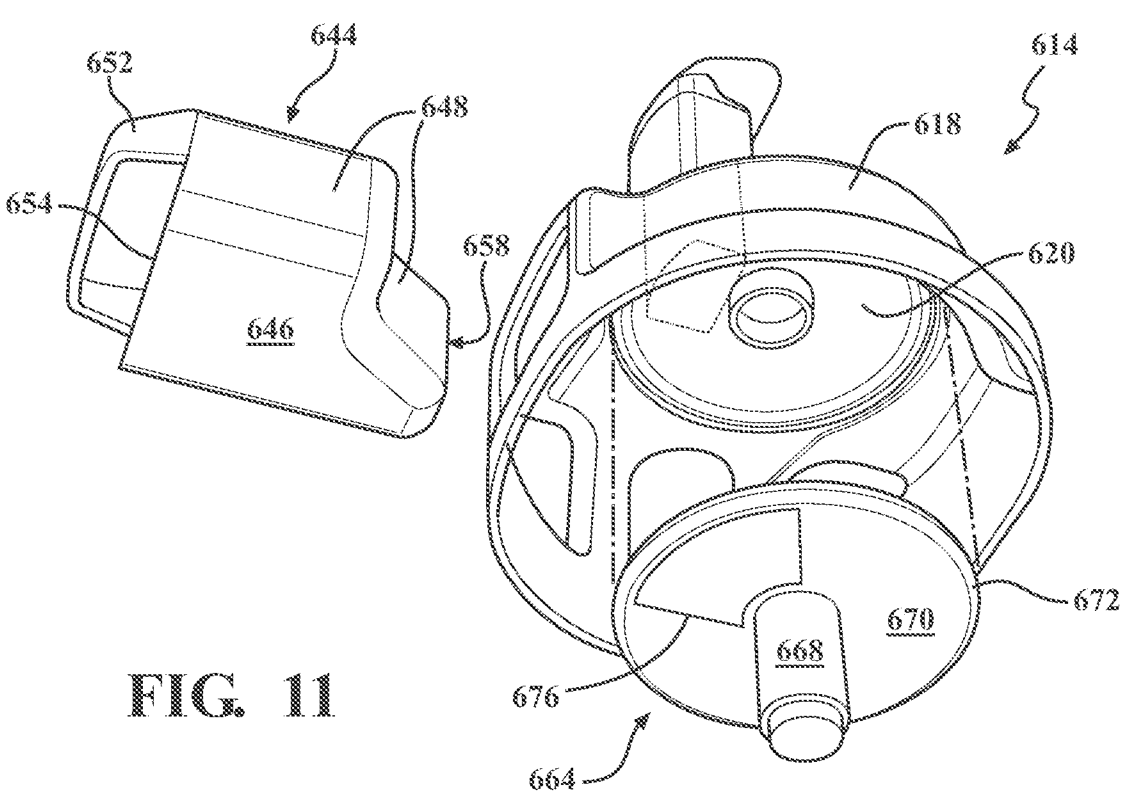
FIG. 11 is a bottom perspective view of the milling module of FIG. 9 having the catch tray removed therefrom.

The milling module 614 of FIGS. 9-11 includes the shell comprising the body 618 and the lid 620 and also includes the catch tray 644. The catch tray 644, described in FIGS. 10 and 11, has a base 646 from which panels 648 extend upwardly, including a back panel 658 having a back surface. A handle 652 projects outwardly from a front panel 654, the panel that is visible when the catch tray 644 is disposed in the milling module 614. The handle 652 functions as the portion of the catch tray 644 that the user grasps to insert the catch tray 644 into the milling module 614 and remove the catch tray 644 from the milling module 614. Once the catch tray 644 is mounted in the milling module 614, various mechanisms can be employed to further secure or hold the catch tray 644 in the milling module 614.

In some examples, the milling module 614 includes a blade retainer 664. The blade retainer 664 can be removed from the milling module which enables the collection of residual bone that remains within the milling module 614 and on the milling element 622 after use. As such, the blade retainer 664 allows efficiency and optimization of bone chip yield as it provides a user-friendly configuration to recover residual milled bone chips. In FIGS. 9-11, a blade retainer 664 includes an upper tray 666 that is circular in shape, and a central sleeve 668. The blade retainer 664 is removably attached to the body 618 of the shell. The central sleeve 668 is concentric with the center of the upper tray 666 and circular in shape. The central sleeve 668 extends downwardly from the upper tray 666. The system 10 is designed so that when the milling module 614 is attached to the base module 12, an opening and the central sleeve 668 are coaxial with the drive spindle. Further, the upper tray 666 includes an upper surface 670 having a void 676 therein and a side wall 672 positioned about an outer circumference of the upper surface 670 and extending upwardly therefrom. During the milling process, milled bone chips pass through the void 676 and into the catch tray 644. The side wall 672 includes one or more tabs 674 that project radially outwardly from the side wall 672. The one or more tabs 674 are positioned and dimensioned so that when the blade retainer 664 is positioned within the body 618 and rotated, each of the tabs 674 rotate out of a respective notch (not illustrated) in the body 618 to remove the blade retainer 664 to facilitate easy access to any residual bone chips which may be disposed on the upper surface 670 of the upper tray 666 and the milling element 622.

In other words, the blade retainer 664 is internal to, and removably attached to, the body 618 of the shell. The central sleeve 668 acts as a handle and when the milling module 614 is removed from the base module, a user can rotate the blade retainer 664 in a first direction and thereby rotationally engage each of the one or more tabs 674 in each of the corresponding notches in the body to retain the milling element 622 in the milling module 614. Further, central sleeve 668 of the blade retainer 664 can be rotated in a second direction, which is opposite the first direction, and thereby rotationally disengage each of the one or more tabs 674 in each of the corresponding notches in the body to allow subsequent removal the blade retainer 664 from the body and therefor facilitate easy access to any residual bone chips which may be disposed on the upper surface 670 of the upper tray 666 and the milling element 622.

The blade retainer 664 is movably mounted to the shell and configured to move from an engaged position to a disengaged position. In the engaged position, the blade retainer 664 cooperates with the body 618 to retain the milling element 622 in the shell such that the milling module 614 is configured to receive power from the motor when attached to the base module. In the disengaged position the blade retainer 664 and the milling element 622 can be removed from the milling module 614 so that residual bone chips can be harvested from the blade retainer 664 and the milling element 622 after the milling process to increase bone chip yield. Referring now to FIG. 9, removal of the blade retainer 664 is illustrated; at arrow $F_{1-6}$ rotational force is applied to disengage the tabs 674 from the notches, and at arrow $F_{2-6}$ the blade retainer 664 is removed from the milling module 614.

In many examples, at least one of the shell 16, the body 18, and the lid 20 is transparent. Transparent elements can allow a user to observe the milling progress when the system 10 is in use and also observe residual bone chips that may be contained in the milling module 14 when the milling process is complete.

The subject disclosure also includes a method of converting bone stock into bone chips. A first example method 700 can be employed with the with the example systems and the exemplary base modules and the milling modules described herein. The system of this disclosure may be prepared for use by connecting the base module to a power supply. The milling module is fitted over the top surface of the base module and attached thereto. The seating of the tabs in the openings releasably holds the milling module static to the base module. Prior to, during, or after the step of attaching the milling module to the base module the lid is attached to the milling module and the locking element of the milling module is moved to a locked position relative to the lid to prevent removal of the lid from the body. In one example, the milling module is attached to the base module with the lid attached to the milling module and the locking element of the milling module in the locked position. Once the milling module is attached, the lid and the catch tray are checked to make sure that they are correctly attached and seated. Once the lid and the catch tray are correctly mounted in place, the system of this disclosure is ready for use.

Figure 12:
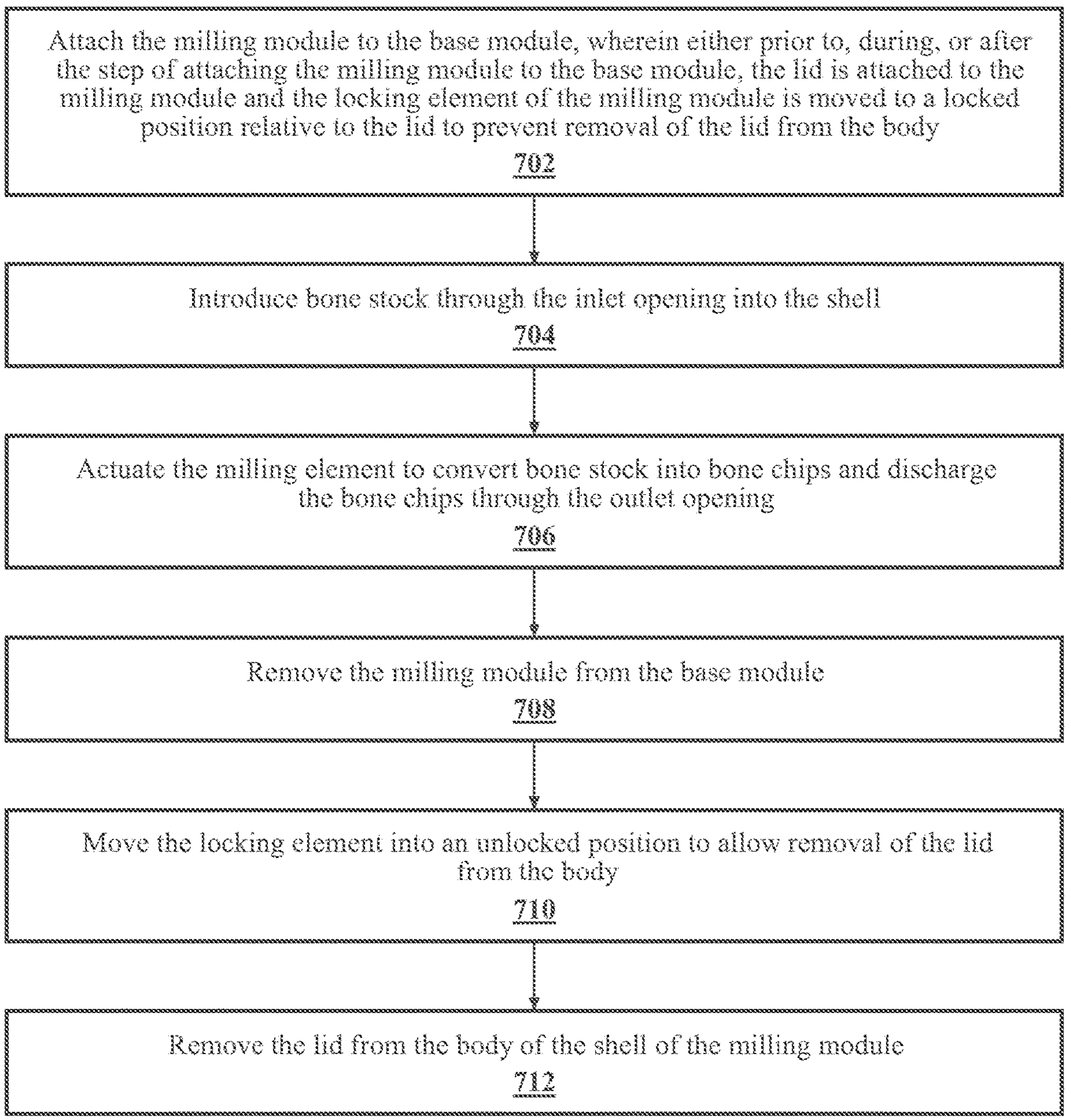
FIG. 12 is a flow diagram illustrating a method of converting bone stock into bone chips with a modular system including a base module and a milling module.

Referring now to FIG. 12, the method 700 includes the steps of: attaching the milling module to the base module 702, wherein either prior to, during, or after the step of attaching the milling module to the base module, the lid is attached to the milling module and the locking element of the milling module is moved to a locked position relative to the lid to prevent removal of the lid from the body; introducing bone stock through the inlet opening into the shell 704; actuating the milling element to convert bone stock into bone chips and discharge the bone chips through the outlet opening 706; removing the milling module from the base module 708; moving the locking element into an unlocked position to allow removal of the lid from the body 710; and removing the lid from the body of the shell of the milling module 712.

In some examples, the system and/or the milling module includes a passive locking configuration because the attachment of the milling module to the base module forces the locking element (e.g. locking shaft) into the locked position to prevent removal of the lid from the body. In such methods, the step of attaching the milling module to the base module 702 forces the locking element into engagement with the lid.

In other examples, the system and/or the milling module includes an active locking configuration because the milling module must first be detached from the base module, and then a force must be applied to the locking element (e.g. locking shaft) to move the locking element into the unlocked position to allow removal of the lid from the body. In some such methods, the step of moving the locking element into an unlocked position to allow removal of the lid from the body 710 further includes exerting a force on the locking element to disengage the locking element from the lid subsequent to the step of removing the milling module from the base module.

Subsequent to the step of removing the milling module from the base module 708, the method 700 may further include the step of removal of the blade retainer. In some examples, rotational force is applied to disengage the blade retainer from the shell and the blade retainer is the removed from the milling module. The blade retainer may facilitate easy access to any residual bone chips which may be disposed on the upper surface of the tray and the milling element.

The method 700 may further include the step of harvesting residual bone chips from interior surfaces of the body and the milling element once the lid and/or the blade retainer is removed from the body. The method 700 may further include the step of removing the milling element from the milling module and harvesting residual bone stock and/or bone chips from surfaces thereof.

The system 10 and method 700 of this disclosure provides a means to use bone chips that while formed, would otherwise not be accessible for use. This feature can also reduce the overall size of the bone stock the practitioner needs to harvest from the patient in order to supply the necessary volume of bone chips for the procedure. This reducing of the volume of the bone stock harvested serves to result in a like reduction in the trauma to which the patient is exposed as a result of the need to have to harvest the bone chips.

Figure 13:
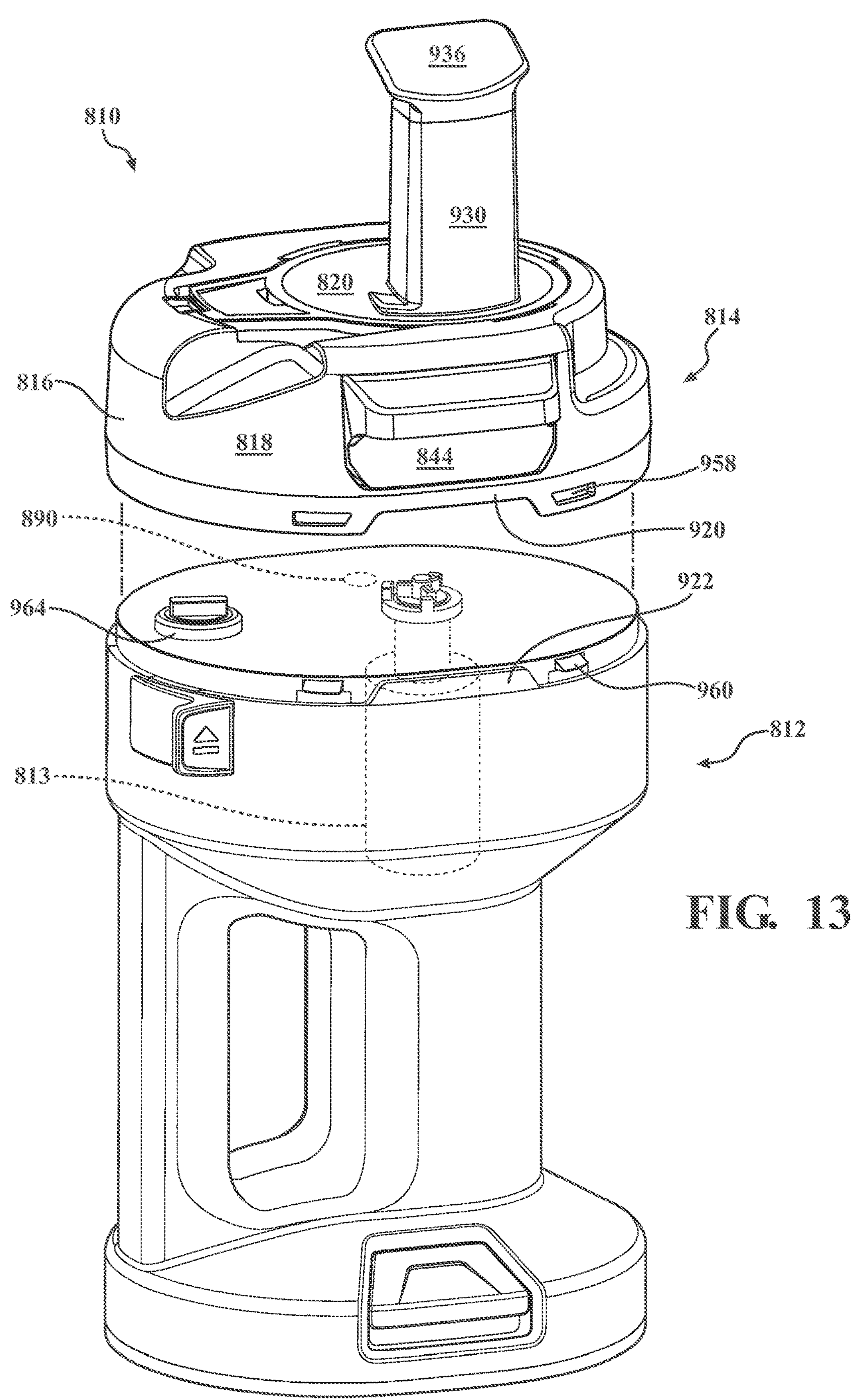
FIG. 13 is an exploded perspective view of another example of a modular system for converting bone stock into bone chips including a base module and a milling module.

FIG. 13 is an exploded perspective view of another example of a modular system 810 for converting bone stock into bone chips including a base module 812 and a milling module 814. FIGS. 13-21 provide various perspective views of the milling module 814. The milling module 814 includes a shell 816 adapted for removable attachment to a base module 812 including a motor 813. The shell 816 defines an inlet opening (not illustrated as the inlet opening is found on the lid 820 at the base of the feed sleeve 930) through which bone stock is introduced into the shell 816, and, in this example, an outlet opening 928 through which bone chips are discharged from the shell 816 and into a catch tray 844. The shell 816 includes a body 818, a milling element 822, a lid 820, and a locking element 824. The milling element 822, which converts bone stock into bone chips, is movably disposed in the shell 816. The lid 820 is shaped for removable attachment to the body 818 to allow removal of residual bone chips from the milling element 822. The locking element 824 is movable between an unlocked position and a locked position. In the unlocked position, the locking element 824 is positioned relative to the lid 820 to allow removal of the lid 820 from the body 818. In the locked position, the locking element 824 is positioned relative to the lid 820 to prevent removal of the lid 820 from the body 818.

Figure 14:
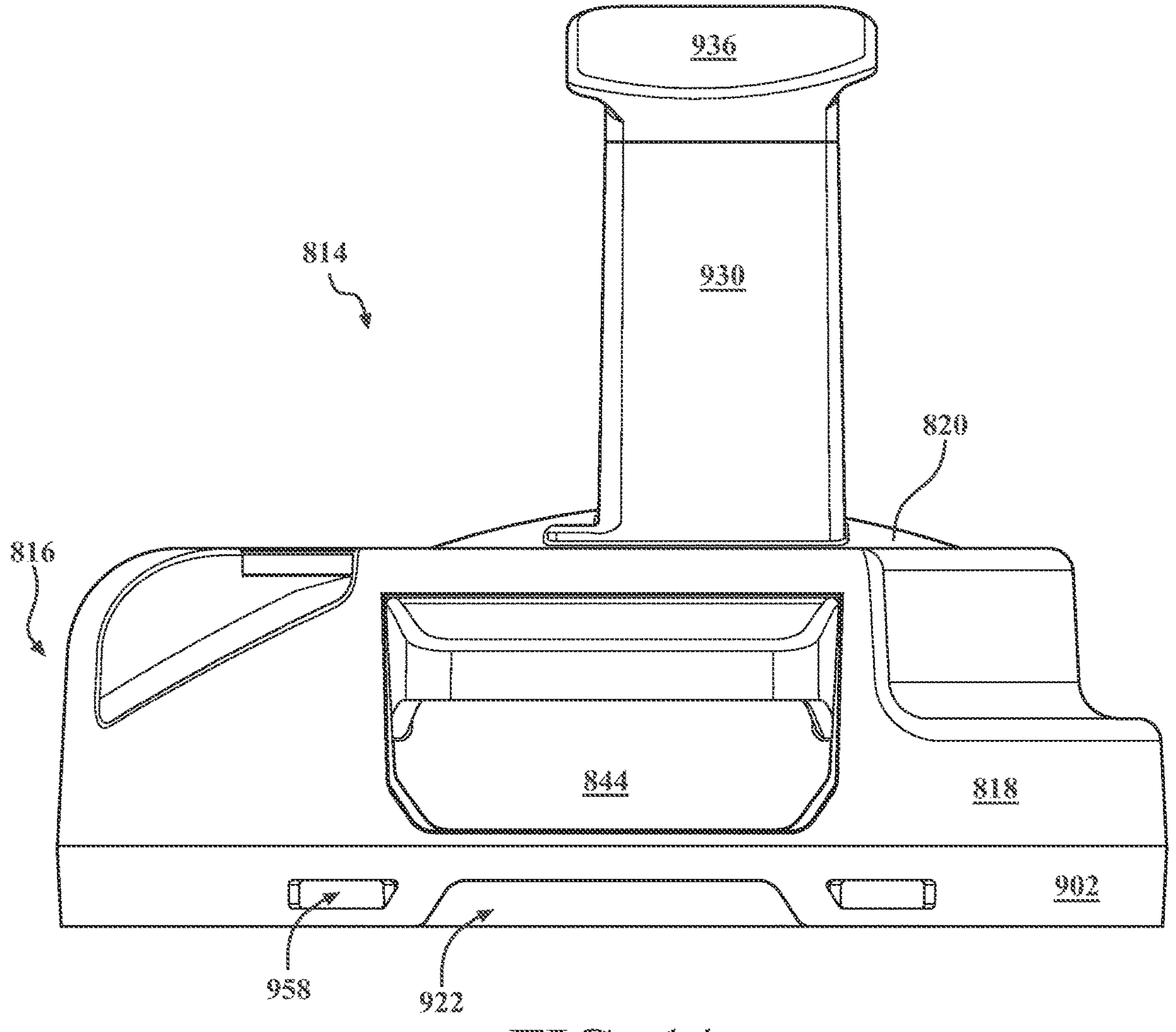
FIG. 14 is an isolated side view of the milling module of FIG. 13.
Figure 15:
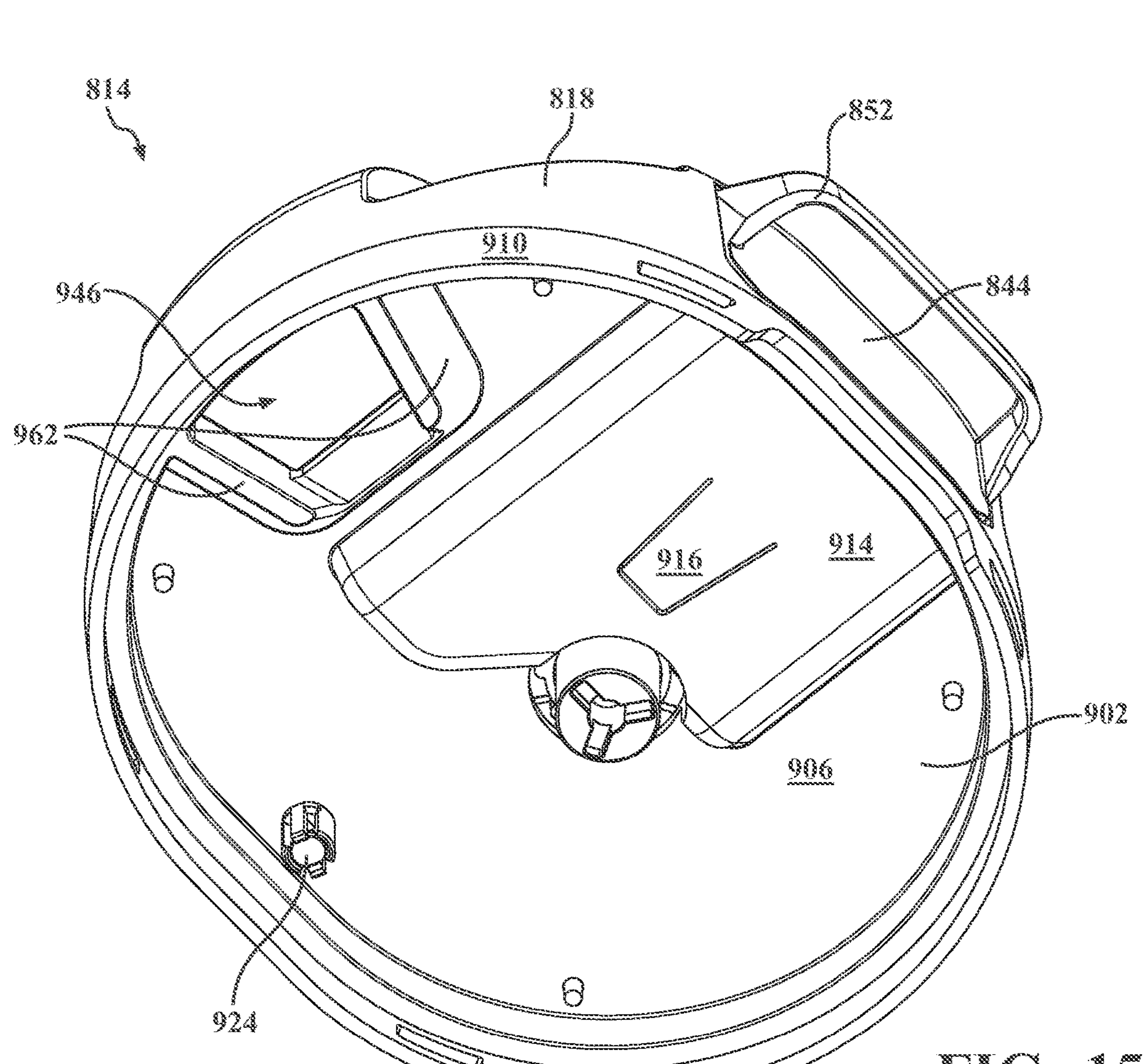
FIG. 15 is an isolated bottom view of the milling module of FIG. 13.

FIG. 15 is an isolated side view of the milling module 814 of the modular system for converting bone stock illustrated in FIG. 13. In this example, the milling module 814 includes a catch tray 844. The catch tray 844 is disposed in an opening 900 (which is not visible in FIG. 13 because the catch tray 844 is disposed in the opening, but is visible in FIG. 16) in the body 818. The catch tray 644, which is illustrated in the isolated view of FIG. 16, has a base 846 from which panels 848 extend upwardly, including a back panel 858 having a back surface. A handle 852 projects outwardly from a front panel 854, which is visible when the catch tray 844 is disposed in the milling module 814 as is illustrated in FIG. 14. The handle 852 functions as the portion of the catch tray 844 that the user grasps to insert the catch tray 844 into the milling module 614 and remove the catch tray 844 from the milling module 614. Once the catch tray 644 is mounted in the milling module 814, various mechanisms can be employed to further secure or hold the catch tray 844 in the milling module 814.

Figure 16:
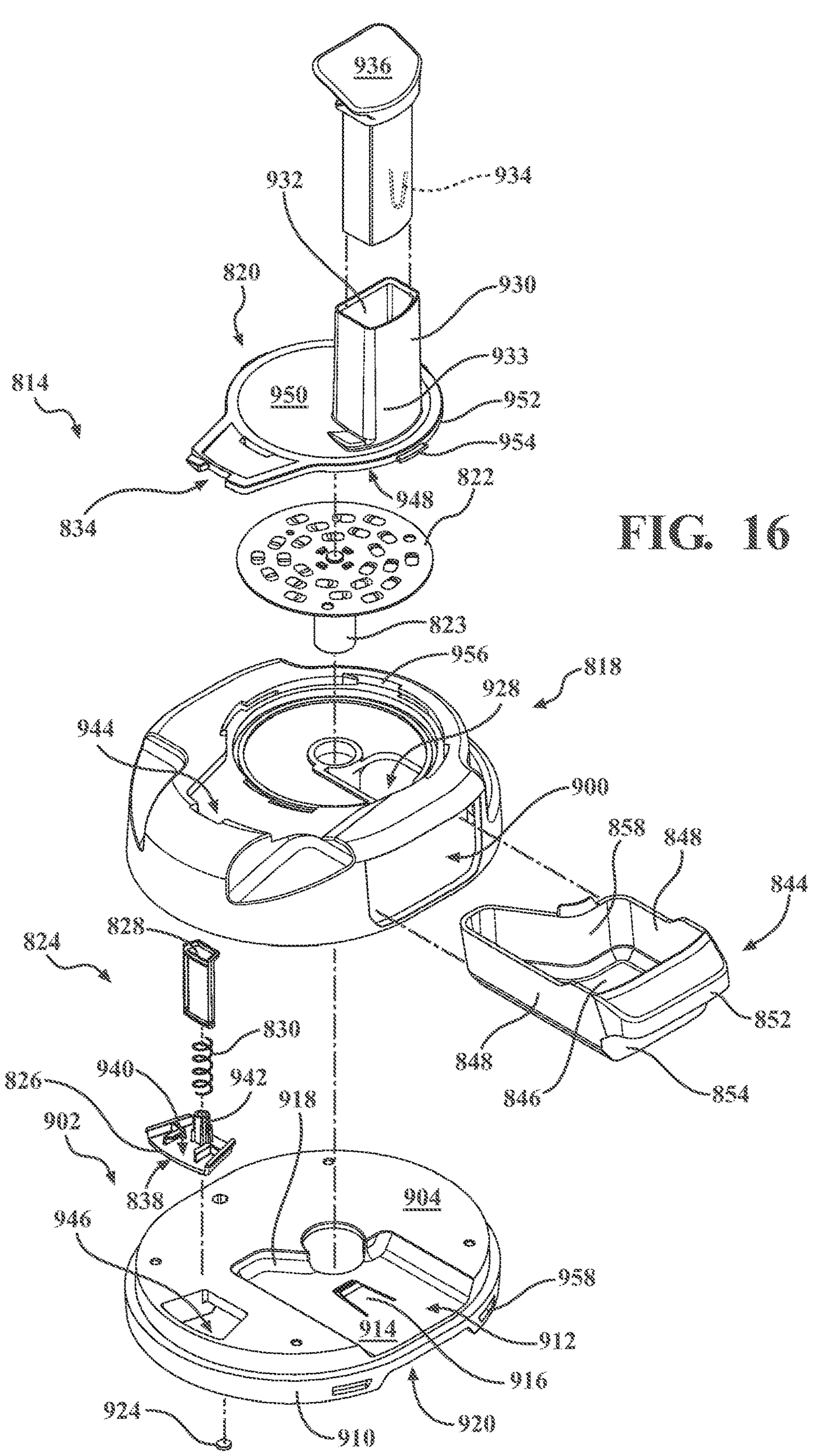
FIG. 16 is an exploded view of the milling module of FIG. 13.

In the examples of FIGS. 13-21, the body 818 of the shell 816 further includes a base plate 902 having a top surface 904, a bottom surface 906, and an exterior wall 910 that extends about the periphery of the bottom surface 906. The top surface 904 of the base plate 902 defines a depression 912 having a floor 914, the opening 900 and the depression 912 are configured to receive the catch tray 844. The top surface 904 of the base plate 902 is illustrated in FIG. 16, whereas the bottom surface 906 and the exterior wall 910 of the base plate 902 are illustrated in FIG. 15. The base plate 902 includes a first retention element 916 that is configured to engage a corresponding retention element on the catch tray 844 to bias the catch tray 844 towards a back wall 918 of the depression 912 to mount the catch tray 844 to the shell 816. In this example, the first retention element 916 is a cut-out retention tab having a projection on the floor 914 of the base plate 902 and the corresponding retention element is a notch on the base 846 of the catch tray 844. The cut-out retention tab and notch can also be referred to as a flexible detent. Of course, this arrangement can be reversed, with the first retention element 916 being a cut-out retention tab on the base 846 of the catch tray 844, and the corresponding retention element being a notch on floor 914 of the base plate 902. Likewise, the cut-out retention tab could define a notch and the second retention element could be a projection.

Further, in this particular example, the exterior wall 910 of the base plate 902 defines an alignment guide 920. The alignment guide 920 is shaped in the exterior wall 910 to receive an alignment tooth 922 on the base module 812, the alignment guide configured to align the milling module 814 with the base module 812 and facilitate efficient and proper attachment of the milling module 814 to the base module 812. In other words, the alignment guide 920 is shaped to receive the alignment tooth 922 on the base module 812, the alignment guide 920 is configured to align the milling module 814 with the base module 812 and facilitate efficient and proper attachment of the milling module 814 to the base module 812. Once the milling module 814 and the base module 812 are aligned, attachment of the milling module 814 to the base module 812 occurs when a plurality of openings 958 on the exterior wall 910 of the base plate 902 receive corresponding tabs 960 on the base module 812.

Further, in this example, the base plate 902 has a magnet 924 mounted thereon. The magnet 924 is detectable by a sensor 890 in the base module 812 when the milling module 814 is attached to the base module 812. The sensor is positioned on the base module 812 to monitor the presence of the magnet 924 and generate a sensor signal for the controller, which is configured to regulate the motor 813 based on the presence of the magnet 924. Of course, if the controller on the base module 812 indicates that the milling module 814 is attached to the base module 812, the controller can control actuation of the motor 813 to ensure optimal process parameters, e.g. speed (rpm) and processing time (seconds) for bone milling. Likewise, if the base module 812 detects that a different module, e.g. a preparation module, is attached to the base module 812, then the controller can control actuation of the motor 813 to ensure optimal process parameters, e.g. speed (rpm) and processing time (seconds) for bone cleaning. In some examples, the controller is configured to work with the sensor to detect attachment of a module, e.g. the milling module 814 or a preparation module for safety purposes.

Referring now to FIG. 14, which is an isolated side view of the milling module 814 of the modular system 810 for converting bone stock illustrated in FIG. 13, the lid 820 of the milling module 814 defines the inlet opening, which is not visible, because a feed sleeve 930 is disposed about the inlet opening. The feed sleeve 930 has an interior surface 932 and an exterior surface 933 and is dimensioned to slidably receive a plunger 936. Referring now to FIG. 16, the plunger 936 includes a second retention element 934 configured to engage a corresponding retention element on the feed sleeve 930 to bias the plunger 936 towards the inlet opening and to engage the plunger 936 within the feed sleeve 930. In this example, the second retention element 934 is a cut-out retention tab on the plunger 936, and the corresponding retention element is a notch on the interior surface 932 of the feed sleeve 930. The cut-out retention tab and notch can also be referred to as a flexible detent. Of course, this arrangement can be reversed, with the second retention element 934 being a cut-out retention tab on the feed sleeve 930, and the corresponding retention element being a notch on the plunger 936. Likewise, the cut-out retention tab could define a notch and the second retention element could be a projection. In this example, the flexible detent is located on a side surface of the plunger 936 opposite the locking recess 834 so that the plunger 936 is biased towards the impingement plate side of the shell 816 so that bone stock does not get stuck between the opposite side surface of the plunger 936 and the interior surface 932 of the feed sleeve 930.

Figure 17:
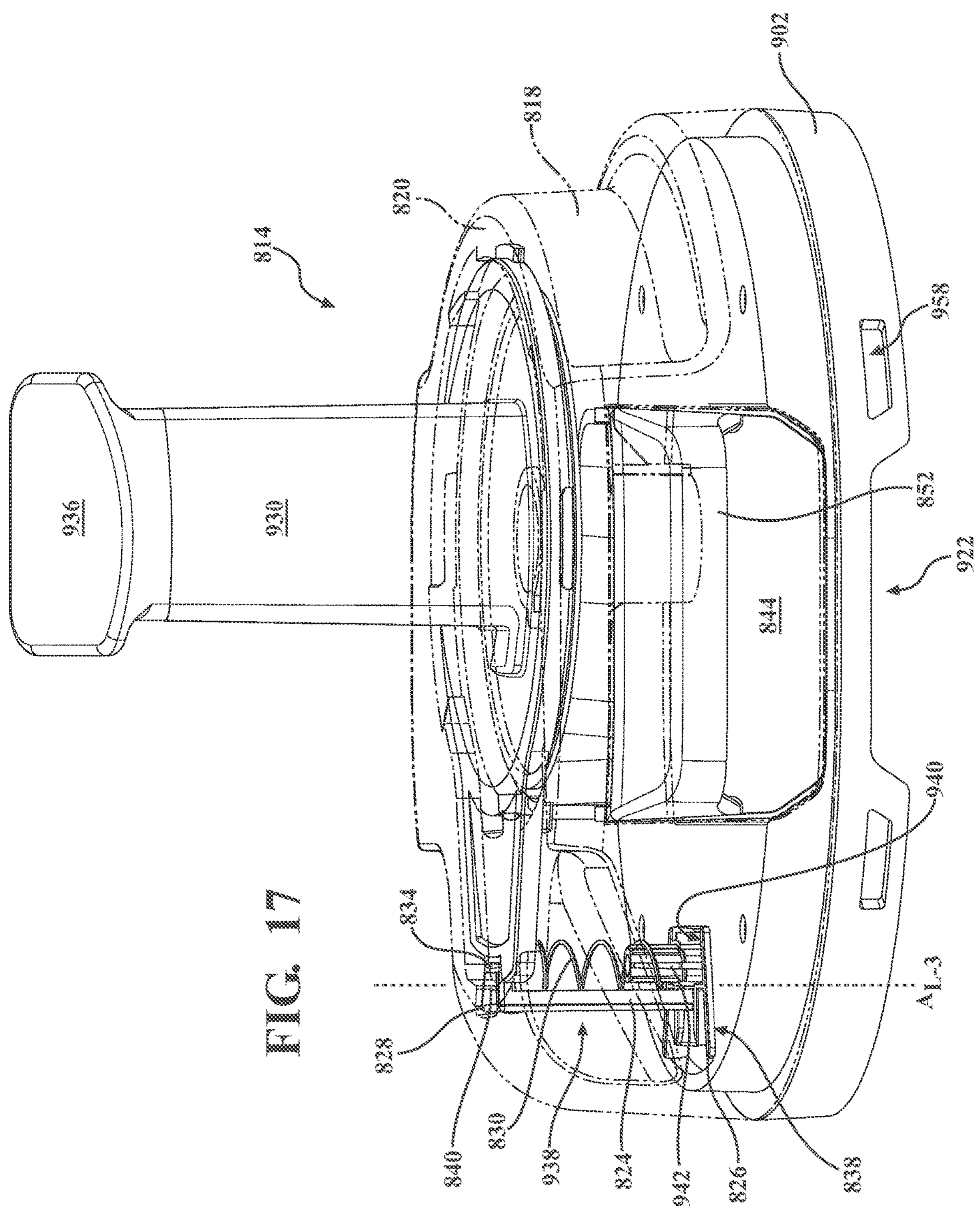
FIG. 17 is an isolated side view of the milling module of FIG. 13 having a body made transparent.

Referring now to FIGS. 17-20, the locking element 824 is shown at 824. In this example, the locking element 824 defines a longitudinal axis $A_{L-3}$ and includes a control surface 838 at a first end 826 and a locking portion 840 at a second end 828. As is best illustrated in FIG. 17, which is a side view of the milling module 814 with the body 818 made transparent, the body 818 defines a channel 938 and the locking element 824 is at least partially disposed within the channel 938. The locking element 824 is movably mounted to the body 818 and coupled to a biasing element 830. The biasing element 830 cooperates with a surface on the lid 820 and/or the body 818 to bias the locking element 824 in a first direction along the longitudinal axis $A_{L-3}$.

In some examples, such as those previously illustrated, the biasing element 830 is disposed about an outer circumference of the locking element 824, the body 818 defines a chamber, and the locking element 824 is movably disposed in the chamber. The body 818 may even include an actuation guide, e.g. a sleeve, with the locking element 824 is at least partially disposed in the actuation guide.

In the example illustrated in FIG. 17, the biasing element 830 is disposed adjacent the locking element 824. In this example, the lid 820 defines a locking recess 834 and the locking element 824 is movable between: the unlocked position, wherein the locking portion 840 is not received within the locking recess 834 in the lid 820 to allow removal of the lid 820 from the body; and the locked position, wherein the locking portion 840 is received within the locking recess 834 in the lid 820 and the locking element 824 prevents removal of the lid 820 from the body 818. In this example, the locking portion 840 includes a foot that is configured to be received within the locking recess 834 in the lid 820. Once the milling module 814 is removed from the base module 812, a force $F_{1-7}$ exerted on the control surface 838 removes the foot from the locking recess 834 to allow rotation and removal of the lid 820 from the body 818.

As is illustrated in FIG. 17, a biasing surface 940 is located adjacent the second end 828 of the locking element 824. The biasing surface 940 is opposite the control surface 838. The biasing surface includes a biasing element mount 942. In this example, the biasing element 830 is disposed about the biasing element mount 942 and abuts an inner surface of the body 818 thereby biasing the locking element 824 in a first direction along the longitudinal axis $A_{L-3}$ towards the base module 812.

With reference to the exploded view of FIG. 16 and the view of FIG. 17, the body 818 defines a channel 938 extending between a locking opening 944 and a control opening 946, wherein the locking element is at least partially disposed within the channel 938. In this example, the first end 826 of the locking element 824 sits in the control opening 946 and the locking portion in the second end 828 of the locking element 824 is moveably disposed in (goes through) the locking opening 944. As was set forth previously, the body 818 of the shell 816 further includes the base plate 902. As is illustrated in FIGS. 15 and 16, the base plate 902 defines the control opening 946. The bottom surface of the base plate includes a module retention element 962. The module retention element 962 extends from the bottom surface 906 and defines a void to engage a boss 964 on the base module 812 and dissipate rotational energy when the milling module 814 is in use. The module retention element 962 may be formed from a one or more ribs spaced apart from one another and partially defining the void. In this example, the module retention element 962 comprises two ribs for engaging a boss 964 on the base module 812. The module retention element 962 is configured to engage the boss 964 and help dissipate rotational energy when the bone mill is in use, i.e. the milling module 814 is on the base module 812 and being actuated.

Figure 18:
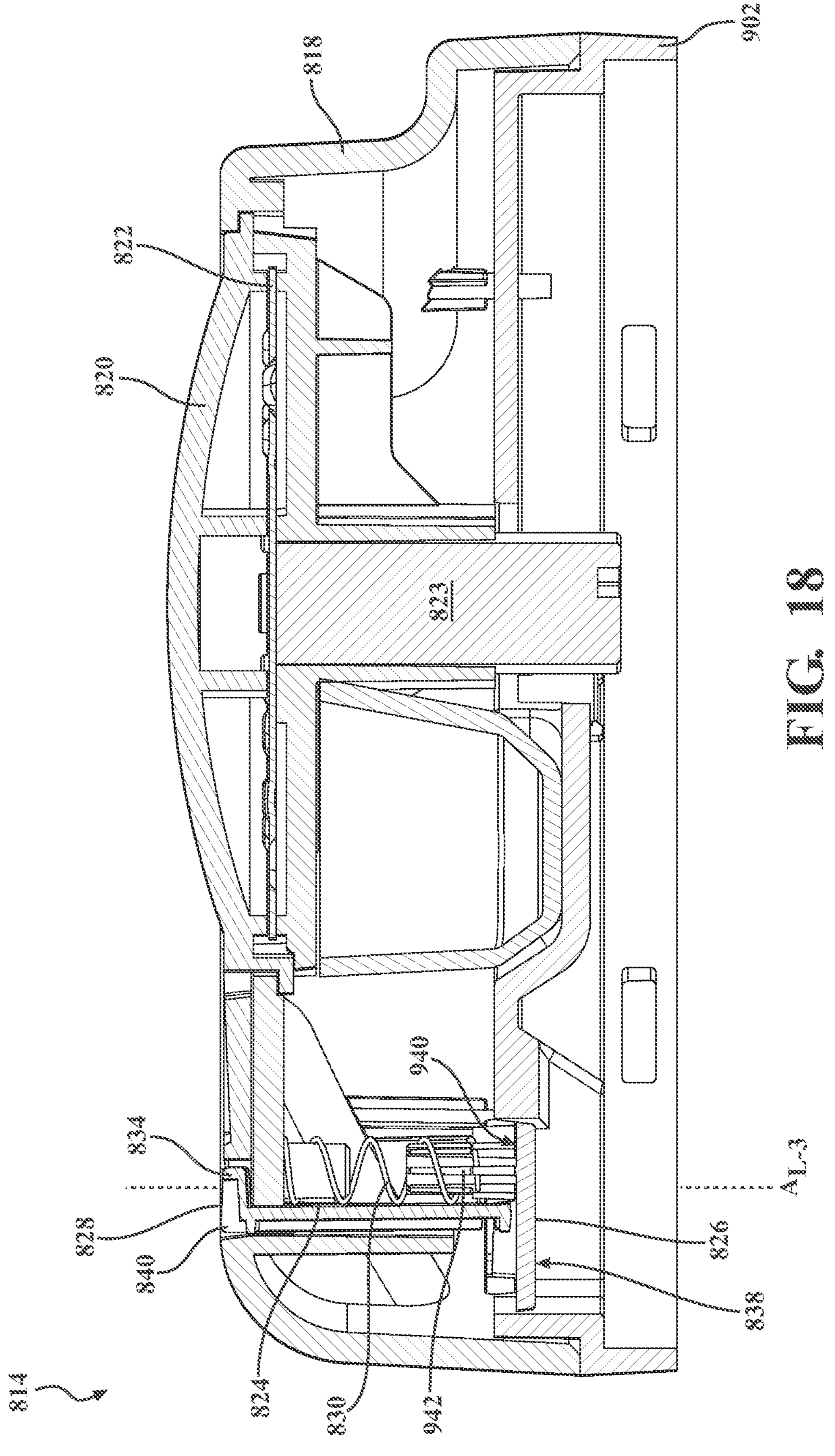
FIG. 18 is a partial, cross sectional view of the milling module of FIG. 17 including a lid and a locking element in a locked position preventing removal of the lid from the body.
Figure 19:
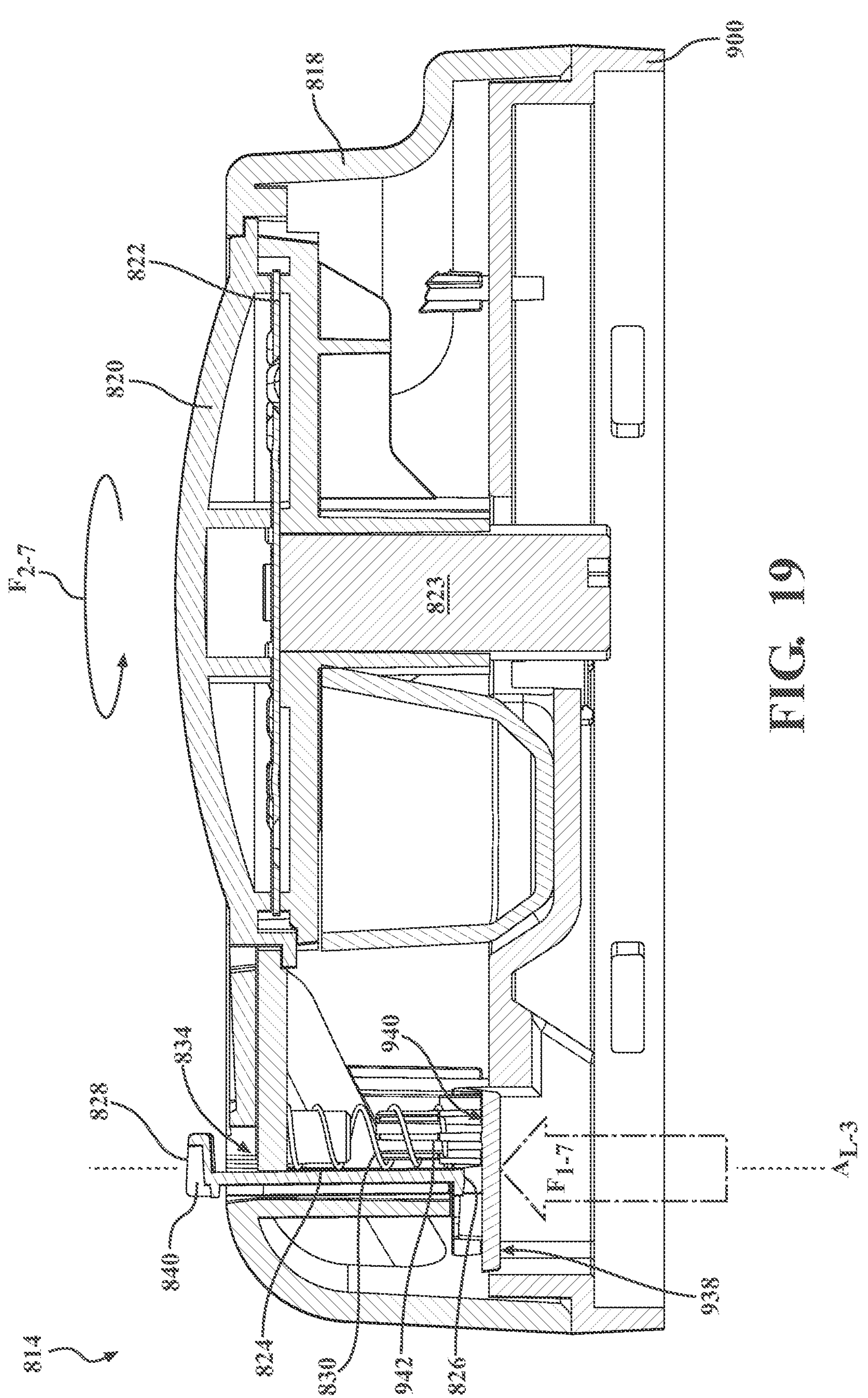
FIG. 19 is a partial, cross sectional view of the milling module of FIG. 18 with a force applied to the locking element for removal of the lid.

Functionally, the locking element 824 includes the control surface 838 located at the first end 826 of the locking element 824 and the locking portion 840 (e.g. foot) at the second end 828 that is configured to be received within the locking recess 834 of the lid 820. A force $F_{1-7}$ can be exerted on the control surface 838 to move the locking element 824 to remove the locking portion 840 from the locking recess 834 and move the locking element 824 from the locked position to the unlocked position to allow subsequent removal of the lid 820 from the body 818. FIG. 18 illustrates the locking element 824 in the locked position. That is, the locking portion 840 of the locking element 824 is received within the locking recess 834 in the lid 820 and the locking element 824 prevents the rotation and removal of the lid 820 from the body 818. As is illustrated in FIG. 19, when a force $F_{1-7}$ is applied to the control surface 838, the locking element 824 moves along the longitudinal axis $A_{L-3}$ within the channel 938 in a second direction and the locking portion 840 on the second end 828 of the locking element 824 lifts out of the recess portion in the lid 820 to allow application of rotational force $F_{2-7}$ to the lid 820 and removal of the lid 820. FIG. 19 illustrates the locking element 824 in an unlocked position. That is, the locking portion 840 of the locking element 824 is not received within the locking recess 834 in the lid 820 as the control surface 838 is pushed $F_{1-7}$ and the lid 820 can be rotationally removed $F_{2-7}$ from the body 818.

Figure 21:
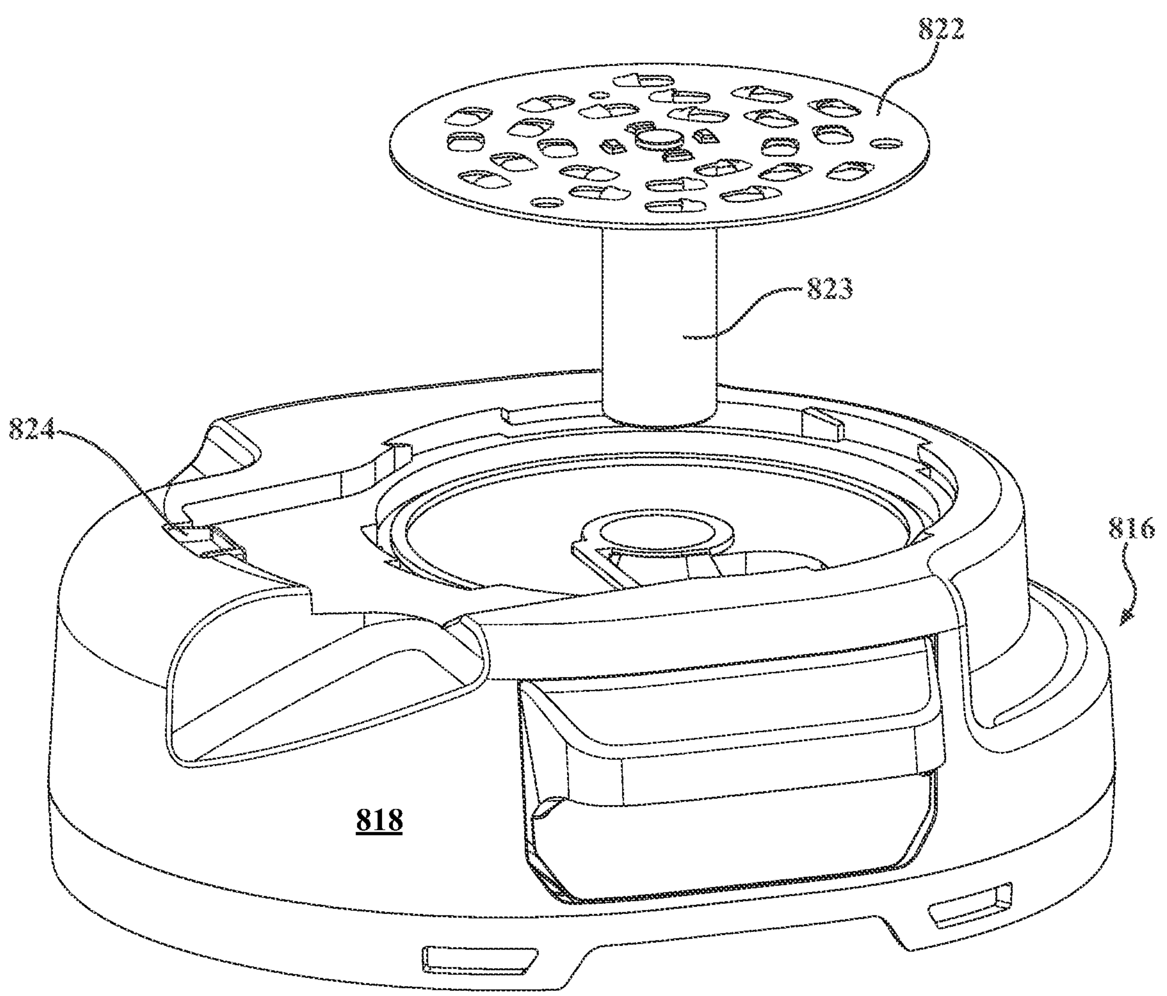
FIG. 21 is a perspective view of the milling module of FIG. 20 with the milling element removed from the body.

Referring now to FIG. 21, the milling module 814 includes the lid 820 which defines the inner surface 948, the outer surface 950, the side wall 952, and the one or more tabs 954 that project radially outwardly from the side wall 952. The one or more tabs 954 are positioned and dimensioned so that when the lid 820 is positioned on the body 818 and rotated, each of the tabs 954 rotate into a respective notch 956 in the body 818 to attach the lid 820 to the body 818. This example prevents rotation of the lid 820 under certain conditions, which prevents removal of the lid 820 from the body 818. In many of the examples herein, the locking element 824 is movable between the locked position in which the lid 820 cannot be removed from the body 818 and an unlocked position where the lid 820 can be removed from the body 818. In the locked position, the locking element

824 prevents rotation of the lid 820. It should be appreciated that the locking element 824 can be attached to: the milling module 814 as described herein; or the base module 812 as is contemplated herein. In this example, a force must be applied to the control surface 838 to allow rotation and consequent removal of the lid 820. However, when the milling module 814 is attached to the base module 812, the control surface 838 is inaccessible for actuation. In the example shown, the control surface 838 is accessible through the control opening 946 in the base plate 902 and cannot be touched by a user unless the milling module 814 is detached from the base module 812. Once the milling module 814 is detached/removed from the base module 812, the control surface 838 is accessible for actuation into the unlocked position so that the lid 820 can be rotationally removed from the body 818.

Figure 20:
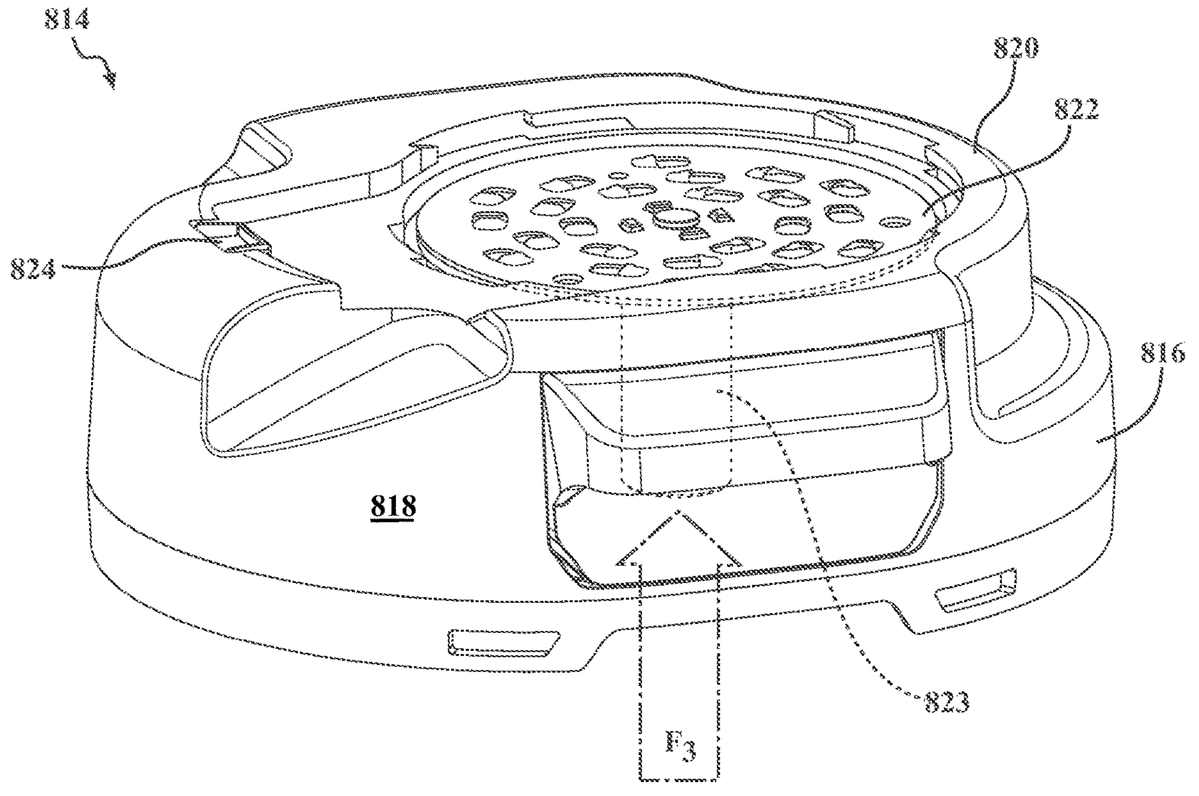
FIG. 20 is a perspective view of the milling module of FIG. 18 with a force applied to the shaft for removal of the milling element.

The removability of the lid 20 makes it possible to access the milling element 822. During use, the milling element converts bone stock into bone chips. Of course the motor 813 in the base module 812 drives the milling element 822 via a drive train. Within this drive train, the drive features releasably couple the milling element 822 to a drive spindle that is accessible through a specific opening in the shell that is present in part for that very purpose. In this example, a shaft 823 transfers the rotational movement of the drive spindle to the milling element 822 so as to rotate the milling element 822 within the shell 816. Referring now to FIGS. 20 and 21, the milling element 822 is adapted for removable attachment to the shell 816. Once the milling module 814 is detached/removed from the base module 812 and the lid 820 is removed from the body 818, the milling element 822 may be removed through an opening in the body 818, which was previously covered by the lid 820. Once the lid 820 is removed from the body 818, the milling element 822 is removed from the shell 816. Using an appropriate tool, such as a scraper, bone chips that adhered to the milling element 822 are scraped off the milling element 822 into the catch tray 844 that holds the bone chips. Further, with the lid 820 off and the milling element 822 in place or removed, bone chips that are adhered to inner surfaces of the body 818 of the milling module 814 can be recovered for use as well. Typically, during this part of the procedure, a user can recover the bone chips that may have otherwise been discarded. In many examples of the disclosure, the shaft is bi-functional. In addition to serving as a drive-link, the shaft functions as the handle that is held when the bone chips that have adhered to the milling element are being recovered. With reference to FIG. 20, once the lid 820 is removed from the body 818, a force $F_3$ is applied to a first end of the shaft which pushes the shaft 823, the milling element 822, and the pin that hold the milling element to the shaft 823, out of a drive sleeve. In FIG. 21, the milling element 822, the shaft 823, and the pin that hold the milling element 822 to the shaft 823 are illustrated as removed from the body 818 of the milling module 814. Once removed, a user can, use the shaft 823 as a handle, and remove residual bone stock from the surfaces of the milling element 822.

In this example, at least one of the shell 816, the body 818, and the lid 820 is partially or totally transparent. Transparent elements can allow a user to observe the milling progress when the system 10 is in use, and also observe residual bone chips that may be contained in the milling module 14 when the milling process is complete. For example, a user could make an observation as to whether or not bone stock is completely milled and/or decide to remove the milling element 822 post milling if residual bone stock is visible through the shell 816, the body 818, and the lid 820.

An alternative example of the milling module 814, with or without the locking element 824, is configured for use with the base module 812 including a motor 813, a controller, and a support surface comprising an alignment tooth 922 and a sensor. In this example, the milling module 814 includes the shell 816 that is adapted for removable attachment to the base module 812, the body 818, and the milling element 822. The shell 816 includes the alignment guide 920 shaped to receive the alignment tooth 922 on the base module 812, the alignment guide 920 is configured to align the milling module 814 with the base module 812 and facilitate efficient and proper attachment of the milling module 814 to the base module 812. The body 818 has a magnet 924 mounted thereto. In a typical example, the magnet 924 is mounted to the bottom surface 906 of the base plate 902. The magnet 924 is detectable by the sensor 890 when the milling module 814 is attached to the base module 812. The sensor 890 is positioned on the base module 812 to monitor the presence of the magnet 924 and generate a sensor signal for the controller, which is configured to regulate the motor 813 based on the presence of the magnet 924. Of course, in this example, the shell 816 may further include the lid 820 shaped for removable attachment to the body 818, and the locking element (as is described in many of the examples above). For example, the locking element 824 may define a longitudinal axis and have a control surface 838 at a first end 826 and a locking portion 840 at the second end 828. The locking element 824 can be positioned to engage the lid 820 when the shell 816 is removably attached to the base module 812. The locking element 824 can be movable between an unlocked position wherein the locking element 824 is positioned relative to the lid 820 to allow removal of the lid 820 from the body 818, and a locked position wherein the locking element 824 is positioned relative to the lid 820 to prevent removal of the lid 820 from the body 818, as is described above. When the locking element 824 is in the locked position, it prevents rotation and subsequent removal of the lid 820 from the body 818.

Of course, in this example, the locking element 824 can be just as described above, with the lid 820 defining a locking recess 834 and the locking element 824 is movable between: the unlocked position wherein the locking portion 840 is not received within the locking recess 834 in the lid to allow removal of the lid 820 from the from the body 818; and the locked position wherein the locking portion 840 is received within the locking recess 834 in the lid 820 and the locking element 824 prevents removal of the lid 820 from the body 818. For example, the milling module 814 may include a foot that is configured to be received within the locking recess 834 in the lid 820. When a force is exerted on the control surface 838, it removes the foot from the locking recess 834 to allow rotation and removal of the lid 820 from the body 818.

With reference to FIGS. 13-21, the modular system 810 for converting bone stock into bone chips includes the base module 812 including a motor 813, and a milling module 814. The milling module 814 includes the shell 816 adapted for removable attachment to the base module 812. The shell includes the body 818, a milling element 822 that is movably disposed in the shell, and the lid 820, which is shaped for removable attachment to the body 818.

The system also includes the locking element 824, that includes the control surface 838 and a locking portion 840. The locking element 824 is movable between a locked position in which the lid 820 cannot be removed and an unlocked position where the lid 820 can be removed. It should be appreciated that the locking element 824 can be attached to: the milling module 814 as described herein; or the base module 812 as is contemplated herein. The locking element 824 can be a stand-alone element which is independent of the base module 812 and the milling module 814. When the milling module 814 is attached to the base module 812, the control surface 838 is inaccessible for actuation and the locking element 824 is in the locked position. When the milling module 814 is not attached to the base module 812, the control surface 838 is accessible for actuation.

In a typical example of the modular system 810, the locking element 824 in the locked position prevents rotation and subsequent removal of the lid 820 from the body 818. As described above, the lid 820 typically defines a locking recess 834 and the locking element 824 is movable between: the unlocked position wherein the locking portion 840 is not received within the locking recess 834 in the lid 820 to allow removal of the lid 820 from the from the body 818; and the locked position wherein the locking portion 840 is received within the locking recess 834 in the lid 820 and the locking element 824 prevents removal of the lid 820 from the body 818.

The locking portion 840 can be shaped and configured in various ways, some of which are described herein, in one example such as that of FIGS. 13-21, the locking portion 840 includes a foot that is configured to be received within the locking recess 834 in the lid 820. When a force is exerted on the control surface, the foot is removed from the locking recess 834 to allow the rotation and the removal of the lid 820 from the body 818.

From a system perspective, a feature described above that can be included on the base module 812 and milling module 814, is the alignment tooth 922 on the base module 812 and the corresponding alignment guide 920 on the milling module 814. The alignment guide 920 is shaped to receive the alignment tooth 922 and configured to align the milling module 814 with the base module 812 and facilitate efficient and proper attachment of the milling module 814 to the base module 812, e.g. make sure that the plurality of openings 958 on the exterior wall 910 of the base plate 902 receive the corresponding tabs 960 on the base module 812. Another feature described above that can be included on the base module 812 and milling module 814, is the magnet 924, which is mounted to the milling module 814. From a system perspective, the base module 812 has a sensor 890 configured to detect the magnet 924 and indicate when the milling module 814 is attached to the base module 812.

In an alternative example, the modular system for converting bone stock into bone chips utilizes a base module 812 including a motor 813, and a milling module 814. The milling module 814 includes a shell 816 adapted for removable attachment to the base module 812. The shell 816 includes a body 818, a milling element 822 for converting bone stock into bone chips movably disposed in the shell 816, and a lid 820 shaped for removable attachment to the body 818. In this example, the modular system 810 includes the locking element 824, but it should be appreciated that the locking element 824 can be attached to the milling module 814 as described herein, or the base module 812, or can be included as a stand-alone element which is independent of the base module 812 and the milling module 814. Of course, the locking element 824, as is described above, is movable between an unlocked position where the locking element 824 is positioned relative to the lid 820 to allow removal of the lid 820 from the body 818, and a locked position wherein the locking element 824 is positioned relative to the lid 820 to prevent removal of the lid 820 from the body 818.

Figure 22:
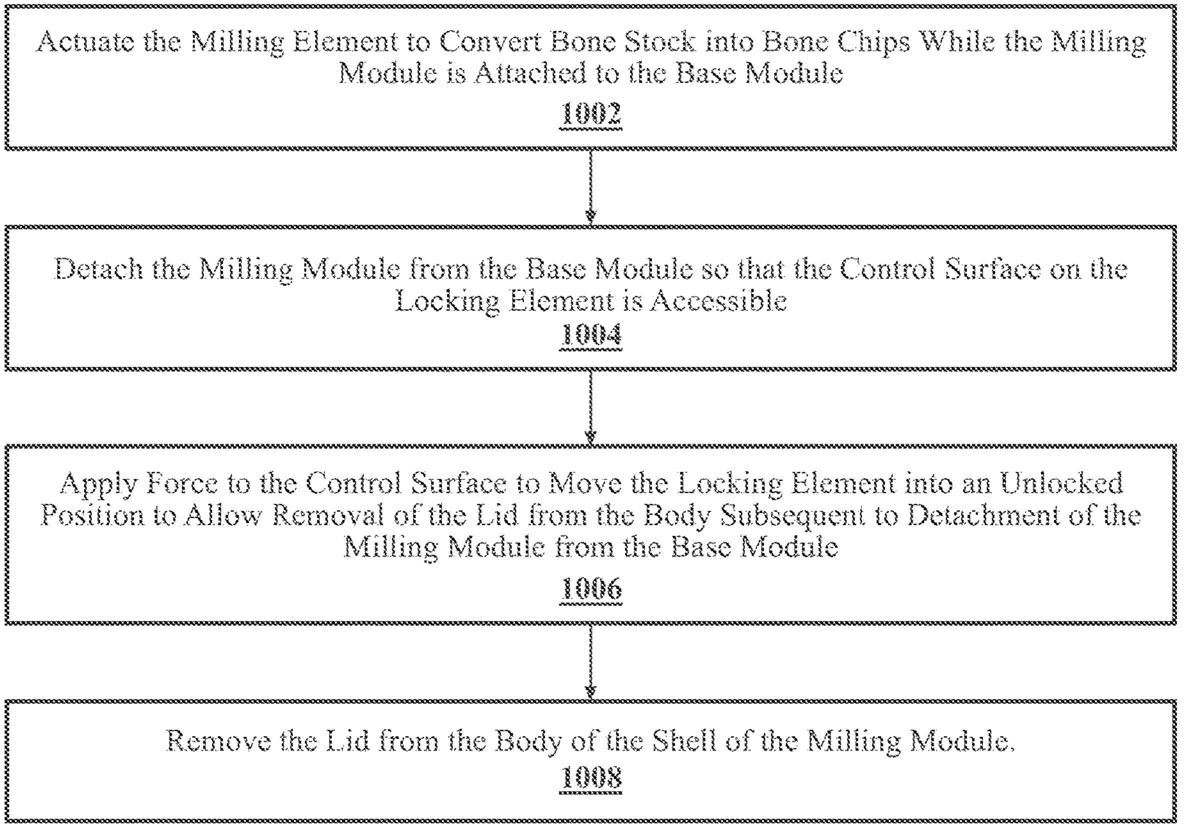
FIG. 22 is a flow diagram illustrating another method of converting bone stock into bone chips with a modular system including a base module and a milling module.

Referring now to FIG. 22, another example of a method 1000 which is associated with, but not limited to, the example of FIGS. 13-22, includes the steps of: actuating the milling element to convert bone stock into bone chips while the milling module is attached to the base module 1002; detaching the milling module from the base module so that the control surface on the locking element is accessible 1004; applying force to the control surface to move the locking element into an unlocked position to allow removal of the lid from the body subsequent to detachment of the milling module from the base module 1006; and removing the lid from the body of the shell of the milling module 1008.

In this method 1000, the step of attaching the milling module to the base module is conducted with the lid attached to the milling module and the locking element of the milling module in the locked position. Once the milling module is attached, the lid and the catch tray are checked to make sure that they are correctly attached and seated. Once the lid and the catch tray are correctly mounted in place, the system of this disclosure is ready for use. Of course, this method may also include the step of providing the milling module, which could be provided as a disposable or even a returnable.

In this example, the system and/or the milling module includes an active locking configuration because the milling module must first be detached from the base module, and then a force must be applied to the locking element (e.g. locking shaft) to move the locking element into the unlocked position to allow removal of the lid from the body. To this end, the step of moving the locking element into an unlocked position to allow removal of the lid from the body further includes exerting a force on the locking element to disengage the locking element from the lid subsequent to the step of removing the milling module from the base module (as is illustrated in FIG. 20). The step of applying force to the control surface to move the locking element into an unlocked position is typically conducted simultaneously with the step of rotating the lid.

Subsequent to the step of removing the lid from the body of the shell of the milling module, the method 1000 may further include the step of harvesting residual bone chips from interior surfaces of the body and the milling element. Plus, the method 1000 may further include the step of removing the milling element from the milling module and harvesting residual bone stock and/or bone chips from surfaces thereof. FIG. 21 illustrates the milling element removed from the milling module.

Of course, the modular system 810 and method 1000 of this disclosure provides a means to use bone chips that while formed, would otherwise not be accessible for use. This feature can also reduce the overall size of the bone stock the practitioner needs to harvest from the patient in order to supply the necessary volume of bone chips for the procedure. This reducing of the volume of the bone stock harvested serves to result in a like reduction in the trauma to which the patient is exposed as a result of the need to have to harvest the bone chips.

Additional Disclosure Clauses:

I. A milling module for converting bone stock into bone chips, the milling module comprising: a shell adapted for releasable attachment to a base module that includes a motor, the shell defining an inlet opening through which bone stock is introduced into the shell and an outlet opening through which bone chips are discharged from the shell, the shell further comprising: a body; a milling element for converting bone stock into bone chips movably disposed in the shell; a lid shaped for removable attachment to the body so that residual bone chips can be removed from the milling element; and a locking element movably mounted to the body and configured to engage the base module and the lid when the shell is releasably attached to the base module, the locking element movable between: an unattached position wherein the locking element is disengaged from the lid such that the lid can be removed from the body; and an attached position wherein the locking element is engaged with the lid to prevent removal of the lid from the body. II. The milling module for converting bone stock into bone chips of clause I, wherein the locking element comprises a locking shaft movably mounted to the body and coupled to a biasing element. III. The milling module for converting bone stock into bone chips of clause II, wherein the biasing element is configured to urge the locking shaft in a first direction such that the locking shaft is biased in a first direction in the unattached position and the locking shaft is pushed in a second direction along a longitudinal axis of the pin in the attached position. IV. The milling module for converting bone stock into bone chips as set forth in clause II or III, wherein the biasing element is disposed about an outer circumference of the locking shaft. V. The milling module for converting bone stock into bone chips as set forth in any preceding clause, wherein the body defines a chamber, the locking element movably disposed in the chamber. VI. The milling module for converting bone stock into bone chips as set forth in any one of clauses II-V, wherein the lid defines a locking recess and the locking shaft is movable between: the unattached position wherein the locking shaft is not received within the locking recess in the lid, and the lid can be removed from the body; and the attached position wherein the locking shaft is received within the locking recess in the lid and the locking shaft prevents removal of the lid from the body. VII. The milling module for converting bone stock into bone chips as set forth in any preceding clause, wherein the lid includes a foundation which defines an inner surface, an outer surface, a side wall, and one or more tabs that project radially outwardly from the side wall, wherein the one or more tabs are positioned and dimensioned so that when the foundation is positioned on the body and rotated, each of the tabs rotate into a respective notch in the body to attach the lid to the body. VIII. The milling module for converting bone stock into bone chips as set forth in clause VII, wherein the locking element in the attached position prevents the rotation and subsequent removal of the lid from the body. IX. The milling module for converting bone stock into bone chips as set forth in clause VIII, wherein the foundation includes a tab and the tab defines the locking recess. X. The milling module for converting bone stock into bone chips as set forth in any preceding clause, wherein the milling element is adapted for releasable attachment to the shell. XI. The milling module for converting bone stock into bone chips as set forth in any preceding clause further comprising a catch tray removably mounted to the shell adjacent the outlet opening to receive bone chips discharged therethrough, wherein the catch tray must be mounted to the shell to actuate the milling element. XII. The milling module for converting bone stock into bone chips as set forth in any preceding clause, wherein at least one of the shell, the body, and the lid is transparent. XIII. A modular system for converting bone stock into bone chips, the system comprising: a base module including a motor and an abutment element; and a milling module comprising: a shell adapted for releasable attachment to a base, the shell defining an inlet opening through which bone stock is introduced into the shell and an outlet opening through which bone chips are discharged from the shell, the shell further comprising: a body; a milling element for converting bone stock into bone chips movably disposed in the shell; a lid shaped for removable attachment to the body; and a locking element movably mounted to the body and configured to engage the base and the lid when the shell is releasably attached to the base, the locking element movable between: an unattached position wherein the locking element disengaged from the lid and the base such that the lid can be removed from the body; and an attached position wherein the locking element is engaged with the base and the lid to prevent removal of the lid from the body, wherein when the milling module is not attached to the base module, the locking element is in the unattached position and the lid can be removed from the body, and wherein when the milling module is attached to the base module, the locking element is in the attached position and the lid is locked in place and cannot be removed from the body. XIV. The modular system for converting bone stock into bone chips as set forth in clause XIII, wherein the locking element comprises a locking shaft movably mounted to the body and coupled to a biasing element thereon. XV. The modular system for converting bone stock into bone chips as set forth in clause XIV, wherein the biasing element is disposed about an outer circumference of the locking shaft. XVI. The modular system for converting bone stock into bone chips as set forth in clause XIV or XV, wherein the lid defines a locking recess and the locking shaft is movable between: the unattached position wherein the locking shaft is not received within the locking recess in the lid and the lid can be removed from the body; and the attached position wherein the locking shaft engaged by the abutment element on the base and received within the locking recess to prevent removal of the lid from the body. XVII. The modular system for converting bone stock into bone chips as set forth in clause XIII, wherein the lid includes a foundation which defines an inner surface, an outer surface, a side wall, and one or more tabs that project radially outwardly from the side wall, wherein the one or more tabs are positioned and dimensioned so that when the foundation is positioned on the body and rotated, each of the tabs rotate into a respective notch in the body to become integral with the notch and attach the lid to the body. XVIII. The modular system for converting bone stock into bone chips as set forth in clause XVII, wherein the foundation includes a locking recess for receiving the locking element, wherein when the locking shaft is in the attached position the locking shaft is received in the locking recess and the lid cannot be rotated and removed from the body. XIX. A method of converting bone stock into bone chips with a modular system including a base module including a motor and an abutment element, and a milling module comprising a shell adapted for releasable attachment to the base module and defining an inlet opening and an outlet opening, the shell comprising a body, a milling element, a lid shaped for releasable attachment to the body, and a locking element movably mounted to the body and configured to engage a base and the lid when the shell is releasably attached to the base, the method comprising the steps of: providing the milling module with the lid attached thereto and the locking element in an unattached position wherein the locking element is disengaged from the lid and the base such that the lid can be removed from the body; and attaching the milling module to the base module wherein the abutment element engages the locking element thereby forcing the locking element to move along a longitudinal axis defined by the locking element and engage with the lid to prevent removal of the lid from the body; introducing bone stock through the inlet opening into the shell; actuating the milling element to convert bone stock into bone chips and discharge the bone chips through the outlet opening; removing the milling module from the base module to disengage the locking element from the lid; and removing the lid from the body of the shell of the milling module. XX. The method of converting bone stock into bone chips as set forth in clause XIX, further comprising the step of harvesting residual bone chips from interior surfaces of the body and the milling element once the lid is removed from the body. XXI. The method of converting bone stock into bone chips as set forth in clause XX, further comprising the step of removing the milling element and harvesting residual bone stock and/or bone chips can be harvested off of surfaces thereof. XXII. A modular system for converting bone stock into bone chips, the system comprising: a base module including a motor; and a milling module comprising: a shell adapted for releasable attachment to a base module that includes a motor, the shell defining an inlet opening through which bone stock is introduced into the shell and an outlet opening through which bone chips are discharged from the shell, the shell further comprising: a body; a milling element for converting bone stock into bone chips movably disposed in the shell; and a lid shaped for removable attachment to the body; wherein the system is configured such that the motor will not power the milling element when the lid is removed from the body. XXIII. The modular system for converting bone stock into bone chips as set forth in clause XXII further comprising a locking element movably mounted to the body and configured to engage the base and the lid when the shell is releasably attached to the base, the locking element movable between: an unattached position wherein the locking element is disengaged from the lid and the base such that the lid can be removed from the body; and an attached position wherein the locking element is engaged by the base and the lid to prevent removal of the lid from the body. XXIV. A milling module for converting bone stock into bone chips, said milling module comprising: a shell adapted for removable attachment to a base module that includes a motor, said shell defining an inlet opening through which bone stock is introduced into said shell and an outlet opening through which bone chips are discharged from said shell, said shell further comprising: a body; a milling element for converting bone stock into bone chips movably disposed in said shell; a lid shaped for removable attachment to said body to allow removal of residual bone chips from said milling element; and a locking element movably mounted to said body and configured to engage said lid when said shell is removably attached to the base module, said locking element movable between: an unlocked position wherein said locking element is positioned relative to said lid to allow removal of said lid from said body; and a locked position wherein said locking element is positioned relative to said lid to prevent removal of said lid from said body. XXV. The milling module for converting bone stock into bone chips of clause XXIV, wherein said locking element is movably mounted to said body and coupled to a biasing element. XXVI. The milling module for converting bone stock into bone chips of clause XXV, wherein said locking element is a locking shaft having a first end and a second end and defining a longitudinal axis. XXVII. The milling module for converting bone stock into bone chips of clause XXVI, wherein said biasing element is configured to urge said locking element in a first direction along said longitudinal axis of said locking element. XXVIII. The milling module for converting bone stock into bone chips of clause XXVI, wherein said biasing element is configured to urge said locking element in a second direction along said longitudinal axis of said locking element. XXIX. The milling module for converting bone stock into bone chips as set forth in clause XXVI, wherein said locking element comprises a biasing surface that cooperates with said biasing element and said body to bias said locking element in a first or a second direction, which is opposite said first direction, along said longitudinal axis of said locking element. XXX. The milling module for converting bone stock into bone chips as set forth in clause XXIX, wherein said biasing surface is located at said first end of said locking element. XXXI. The milling module for converting bone stock into bone chips as set forth in clauses XXIX or XXX, wherein said biasing element is disposed adjacent said locking element. XXXII. The milling module for converting bone stock into bone chips as set forth in clauses XXIX or XXX, wherein said biasing element is disposed about an outer circumference of said locking element. XXXIII. The milling module for converting bone stock into bone chips as set forth in clause XXV, wherein said body defines a chamber, and said locking element and said biasing element are movably disposed in said chamber. XXXIV. The milling module for converting bone stock into bone chips as set forth in clause XXVI, wherein said lid defines a locking recess and said locking shaft is movable between: said unlocked position wherein said locking shaft is not received within said locking recess in said lid to allow removal of said lid from said from said body; and said locked position wherein said locking shaft is received within said locking recess in said lid and said locking shaft prevents removal of said lid from said body. XXXV. The milling module for converting bone stock into bone chips as set forth in clause XXXIV, wherein a chamber is defined by a locking sleeve and said locking shaft and said biasing element are disposed in said locking sleeve, wherein said biasing element is configured to urge a first end of said locking shaft longitudinally past a first end of said locking sleeve. XXXVI. The milling module for converting bone stock into bone chips as set forth in clause XXIV, wherein said shell defines a lower plane opposite said lid and a biasing element is configured to urge a first end of said locking element longitudinally past said lower plane of said shell. XXXVII. The milling module for converting bone stock into bone chips as set forth in clause XXXIV, wherein when said milling module is not attached to the base module, said biasing element is configured to urge said locking shaft into said unlocked position to allow removal of said lid from said body and when attached to the base module, said locking shaft is forced into said locked position to prevent removal of said lid from said body. XXXVIII. The milling module for converting bone stock into bone chips as set forth in clause XXXIV, wherein said locking shaft includes a tab, wherein a force exerted on said tab removes said locking shaft from said locking recess. XXXIX. The milling module for converting bone stock into bone chips as set forth in clause XXXIV, wherein said locking shaft includes a tab located at a first end of said locking shaft and a foot at a second end that is configured to be received within said locking recess in said lid, wherein a force exerted on said tab removes said foot from said locking recess and moves said locking shaft from said locked position to said unlocked position to allow subsequent removal of said lid from said body. XL. The milling module for converting bone stock into bone chips as set forth in clause XXXIV, wherein said locking shaft includes a tab located at a first end of said locking shaft and a foot at a second end that is configured to be received within said locking recess in said lid, wherein a force exerted on said tab removes said foot from said locking recess and moves said locking shaft from said locked position to said unlocked position to allow subsequent removal of said lid from said body. XLI. The milling module for converting bone stock into bone chips of clause XXIV, wherein said locking element comprises a locking arm having a second end and a first end and is pivotably mounted to said body. XLII. The milling module for converting bone stock into bone chips as set forth in clause XLI, wherein said lid defines a locking recess and said locking arm comprises a foot located at said second end which is configured to be received by said locking recess in said lid, a mounting element, and optionally a biasing element. XLIII. The milling module for converting bone stock into bone chips as set forth in clause XLII, wherein said locking arm is biased into a locked position and exertion of a force on said first end of said locking arm pivots said locking arm from said locked position to said unlocked position to allow removal of said lid from said body. XLIV. The milling module for converting bone stock into bone chips as set forth in clause XLIII, wherein the base module includes an abutment element that prevents pivoting of said locking arm into said unlocked position and subsequent removal of said lid from said body when said milling module is attached to the base module. XLV. The milling module for converting bone stock into bone chips as set forth in clause XLIV, wherein said first end of said locking arm includes a tab. XLVI. The milling module for converting bone stock into bone chips as set forth in any preceding clause, wherein said lid defines an inner surface, an outer surface, a side wall, and one or more tabs that project radially outwardly from said side wall, wherein said one or more tabs are positioned and dimensioned so that when said lid is positioned on said body and rotated, each of said tabs rotate into a respective notch in said body to attach said lid to said body. XLVII. The milling module for converting bone stock into bone chips as set forth in clause XLVI, wherein said locking element in said locked position prevents rotation of said lid to prevent removal of said lid from said body. XLVIII. The milling module for converting bone stock into bone chips as set forth in any preceding clause, wherein said milling element is adapted for removable attachment to said shell. XLIX. The milling module for converting bone stock into bone chips as set forth in any preceding clause, further comprising a blade retainer internal to, and removably attached to, said body of said shell, said blade retainer comprising: an upper tray including an upper surface for retaining said milling element in said body that is circular in shape, a side wall positioned about an outer circumference of said upper surface that has one or more tabs that project radially outwardly therefrom; and a central sleeve concentric with a center of said upper tray and extending downwardly from said upper tray; wherein said one or more tabs that project radially outwardly from said side wall are shaped to allow engagement of each of said one or more tabs into a corresponding notch in said body; and wherein rotation of said central sleeve in a first direction rotationally engages each of said one or more tabs in each of the corresponding notches in said body to retain said milling element in said milling module and rotation of said central sleeve in a second direction, opposite said first direction, rotationally disengages each of said one or more tabs in each of the corresponding notches in said body to allow subsequent removal of said blade retainer and said milling element from said body and thereby facilitate easy access to any residual bone chips which may be disposed on said upper surface of said upper tray and said milling element. L. The milling module for converting bone stock into bone chips as set forth in any preceding clause, wherein at least one of said shell, said body, and said lid is transparent. LI. A modular system for converting bone stock into bone chips, said system comprising: a base module including a motor; and a milling module comprising: a shell adapted for removable attachment to the base module, the shell defining an inlet opening through which bone stock is introduced into the shell and an outlet opening through which bone chips are discharged from the shell, the shell further comprising: a body; a milling element for converting bone stock into bone chips movably disposed in the shell; a lid shaped for removable attachment to the body; and a locking element movably mounted to the body and positioned to engage the lid when the shell is removably attached to the base module, the locking element movable between: an unlocked position wherein the locking element is positioned relative to the lid to allow removal of the lid from the body; and a locked position wherein the locking element is positioned relative to the lid to prevent removal of the lid from the body, wherein when the milling module is not attached to the base module, the locking element is in the unlocked position to allow removal of the lid from the body, and wherein when the milling module is attached to the base module, the locking element is in the locked position and prevents removal of the lid from the body. LII. The modular system for converting bone stock into bone chips as set forth in clause LI, wherein the locking element is movably mounted to the body and coupled to a biasing element. LIII. The modular system for converting bone stock into bone chips as set forth in clause LII, wherein the locking element is a locking shaft having a first end and a second end and defining a longitudinal axis. LIV. The modular system for converting bone stock into bone chips as set forth in clause LIII, wherein the biasing element is configured to urge the locking shaft in a first direction along the longitudinal axis of the locking shaft. LV. The modular system for converting bone stock into bone chips as set forth in clause LIII, wherein the biasing element is configured to urge the locking shaft in a second direction along the longitudinal axis of the locking shaft. LVI. The modular system for converting bone stock into bone chips as set forth in clause LIII, wherein the body defines a chamber, and the locking shaft and the biasing element are disposed in the chamber. LVII. The modular system for converting bone stock into bone chips as set forth in clause LVI, wherein the body comprises a sleeve that defines the chamber, and the locking element and biasing element are movably disposed in the sleeve. LVIII. The modular system for converting bone stock into bone chips as set forth in clause LIII, wherein the lid defines a locking recess and the locking shaft is movable between: the unlocked position wherein the locking shaft is not received within the locking recess in the lid to allow removal of the lid from the body; and the locked position wherein the locking shaft is received within the locking recess in the lid and the locking shaft prevents removal of the lid from the body. LIX. The modular system for converting bone stock into bone chips as set forth in clause LVIII, wherein the lid includes a locking tab and the locking tab defines the locking recess. LX. The modular system for converting bone stock into bone chips as set forth in clause LVII or LVIII, wherein the chamber is defined by a locking sleeve and the locking element is disposed in the locking sleeve, wherein the biasing element is configured to urge the first end of the locking shaft longitudinally past a first end of the locking sleeve. LXI. The modular system for converting bone stock into bone chips as set forth in clause LX, wherein the base module is shaped such that when the milling module is attached to the base module the first end of the locking element is engaged with the base module to force the locking shaft into the locking recess and into the locked position. LXII. The modular system for converting bone stock into bone chips as set forth in clause LI, wherein the locking element includes a tab and when the milling module is not attached to the base module a force exerted on the tab moves the locking element into the unlocked position. LXIII. The modular system for converting bone stock into bone chips as set forth in clause LVIII, wherein when the milling module is not attached to the base module, the biasing element is configured to urge the locking shaft into the unlocked position to allow removal of the lid from the body, and wherein when the lid is attached to the base module, the base module is shaped to force the locking shaft into the locked position to prevent removal of the lid from the body. LXIV. The modular system for converting bone stock into bone chips as set forth in clause LVIII, wherein the locking shaft includes a tab located at a first end of the locking shaft and a foot at a second end that is configured to be received within the locking recess in the lid, wherein when the milling module is not attached to the base module, a force exerted on the tab removes the foot from the locking recess and moves the locking shaft from the locked position to the unlocked position to allow subsequent removal of the lid from the body. LXV. The modular system for converting bone stock into bone chips as set forth in clause LVIII, wherein the locking shaft includes a tab located at a first end of the locking shaft and a foot at the second end of the locking shaft that is configured to be received within the locking recess in the lid, wherein when the milling module is not attached to the base module, a force exerted on the tab removes the foot from the locking recess and moves the locking shaft from the locked position to the unlocked position to allow subsequent removal of the lid from the body. LXVI. The modular system for converting bone stock into bone chips for converting bone stock into bone chips of clause LI, wherein the locking element comprises a locking arm having a first end and a second end and is pivotably mounted to the body. LXVII. The modular system for converting bone stock into bone chips for converting bone stock into bone chips as set forth in clause LXVI, wherein the locking arm comprises a foot which is configured to be received by a locking recess in the lid, a mounting element, and optionally a biasing element. LXVIII. The modular system for converting bone stock into bone chips for converting bone stock into bone chips as set forth in clause LXVII, wherein the locking arm is biased into a locked position and exertion of a force on the first end of the locking arm pivots the locking arm from the locked position to the unlocked position to allow removal of the lid from the body. LXIX. The modular system for converting bone stock into bone chips for converting bone stock into bone chips as set forth in clause LXVIII, wherein the base module includes an abutment element and the first end of the locking arm abuts the abutment element, which prevents the pivoting of the locking arm into the unlocked position and subsequent removal of the lid from the body when the milling module is attached to the base module. LXX. The modular system for converting bone stock into bone chips as set forth in clause LI, wherein the lid defines an inner surface, an outer surface, a side wall, and one or more tabs that project radially outwardly from the side wall, wherein the one or more tabs are positioned and dimensioned so that when the lid is positioned on the body and rotated, each of the tabs rotate into a respective notch in the body to become integral with the notch and attach the lid to the body. LXXI. The modular system for converting bone stock into bone chips as set forth in clause LXX, wherein the lid includes a locking recess for receiving the locking element, wherein when the locking element is in the locked position, the locking element is received in the locking recess to prevent removal of the lid from the body. LXXII. A method of converting bone stock into bone chips with a modular system including a base module including a motor, and a milling module comprising a shell adapted for removable attachment to the base module and defining an inlet opening and an outlet opening, the shell comprising a body, a milling element, a lid shaped for removable attachment to the body, and a locking element movably mounted to the body and configured to engage the lid when the shell is removably attached to the base module, said method comprising the steps of: attaching the milling module to the base module, wherein either prior to, during, or after the step of attaching the milling module to the base module, the lid is attached to the milling module and the locking element of the milling module is moved to a locked position relative to the lid to prevent removal of the lid from the body; introducing bone stock through the inlet opening into the shell; actuating the milling element to convert bone stock into bone chips and discharge the bone chips through the outlet opening; removing the milling module from the base module; moving the locking element into an unlocked position to allow removal of the lid from the body; and removing the lid from the body of the shell of the milling module. LXXIII. The method of converting bone stock into bone chips as set forth in clause LXXII, wherein the step of attaching the milling module to the base module is conducted with the lid attached to the milling module and the locking element of the milling module in the locked position. LXXIV. The method of converting bone stock into bone chips as set forth in clause LXXII or LXXIII, wherein the step of moving the locking element into the unlocked position comprises exerting a force on the locking element subsequent to the step of removing the milling module from the base module. LXXV. The method of converting bone stock into bone chips as set forth in clause LXXII, wherein the step of attaching the milling module to the base module is conducted with the lid attached to the milling module, and wherein the step of attaching the milling module to the base module forces the locking element into the locked position to simultaneously move the locking element into the locked position. LXXVI. The method of converting bone stock into bone chips as set forth in clause LXXII, further comprising the step of harvesting residual bone chips from interior surfaces of the body and the milling element once the lid is removed from the body. LXXVII. The method of converting bone stock into bone chips as set forth in clause LXXII, further comprising the step of removing the milling element from the milling module and harvesting residual bone stock and/or bone chips from surfaces thereof.

The foregoing is directed to one specific version of the disclosure. Alternative versions of the disclosure may have different features from what has been described.

For example, there is no requirement that all versions of the disclosure include the detection components and sensor system for determining whether or not the lid 20 and the catch tray 44 are properly attached to the body 18 of the shell 16. Similarly, some versions of this disclosure may not include the catch tray 44.

The features of the disclosure may likewise vary from what has been described. Thus, there is no requirement that in all versions of the disclosure the milling element that converts the bone stock into bone chip be a disc. In some versions of the disclosure, this component may be a blade.

Likewise, in versions of the disclosure in which a sensor monitors whether or not the lid 20 and/or catch tray 44 are properly attached to the milling module 14 may not always be a sensor that monitors the presence/absence of a magnetic field. In some versions of the disclosure, the sensor may be an optical sensor that emits a signal based on whether or not light at a particular wavelength is received. In these versions of the disclosure, the marker integral with the lid 20 may be a reflector. The detection component integral with the catch tray 44 may be an optic fiber with a filter that allows light to pass through at the monitored wavelength. In other versions of the disclosure, the sensor may be a mechanical switch. In these versions of the disclosure, the detection component may be static or moving mechanical components integral with the lid 20 and the catch tray 44. As a result of these components going into registration or engaging, these components actuate the switch. The changing of the state of the signal across the switch is interpreted by the controller as indicating that the lid 20 and the catch tray 44 are properly attached to the milling module 14.

In versions of the disclosure without the catch tray 44, a detection component may be associated with the shell 16. In this version of the disclosure, only if the shell 16 of the system 10 is properly attached to the base module 12 and the lid 20 is properly attached to the shell 16 of the system 10 does the sensor output a signal indicating that these component are properly attached to the base module 12. Only when this signal is received does the controller allow the motor integral with the base module 12 to be actuated.

The system 10 of this disclosure is designed to reduce pieces of material. That is, the system 10 is designed convert a set number of larger pieces of material into a larger number of smaller pieces of material. The system 10 can be configured to reduce hard or soft material, and the system 10 can be configured to produce a particular size the smaller pieces of material. For example, using different milling elements, the system 10 of this disclosure may be used to cut soft tissue into a form in which this tissue can be used in a procedure or convert bone stock into bone particles (rather than bone chips). Further, while this disclosure is focused on the reduction of bone stock into bone chips, the system 10 may have other uses. Also, system 10 may have applications other than in surgery.

Accordingly, it is an object of the appended claims to cover all such variations and modifications that come within the true spirit and scope of this disclosure.

What is claimed is:

1. A milling module for converting bone stock into bone chips, the milling module comprising:

a shell adapted for removeable attachment to a base module that includes a motor, the shell defining an inlet opening through which bone stock is introduced into the shell, the shell further comprising:

a body including a base plate having a top surface, with said base plate defining a control opening and with said body defining a channel extending from said control opening to a lock opening;

a milling element for converting bone stock into bone chips movably disposed in the shell above said base plate and below said inlet opening;

a lid adjacent said lock opening and shaped for removeable attachment to the body to allow removal of residual bone chips from the milling element, wherein said lid defines a locking recess; and a locking element having a control surface with the control surface at least partially seated in the control opening of the base plate within the channel defined by the body inside the shell, the locking element movable via the control surface between:

an unlocked position wherein the locking element is positioned relative to the lid to allow removal of the lid from the body without requiring removal from the base module including the motor; and a locked position wherein the locking element is positioned in said locking recess relative to the lid to prevent removal of the lid from the body;

wherein the control surface is inaccessible for actuation when the milling module is attached to the base module, and wherein the control surface is accessible from an underside of the base plate opposite the top surface for actuation when the milling module is not attached to the base module.

2. The milling module for converting bone stock into bone chips as set forth in claim 1, wherein the locking element defines a longitudinal axis and comprises a control surface at a first end and a locking portion at a second end.

3. The milling module for converting bone stock into bone chips as set forth in claim 2, wherein the locking element is movably mounted to the body and coupled to a biasing element.

4. The milling module for converting bone stock into bone chips as set forth in claim 3, wherein the locking element comprises a biasing surface that cooperates with the biasing element and the body to bias the locking element in a first or a second direction along the longitudinal axis of the locking element.

5. The milling module for converting bone stock into bone chips as set forth in claim 4, wherein the biasing surface is located at the first end of the locking element.

6. The milling module for converting bone stock into bone chips as set forth in claim 3, wherein the biasing element is disposed about an outer circumference of the locking element.

7. The milling module for converting bone stock into bone chips as set forth in claim 3, wherein the biasing element is disposed adjacent the locking element.

8. The milling module for converting bone stock into bone chips as set forth in claim 1, wherein the body defines a chamber and the locking element is movably disposed in the chamber.

9. The milling module for converting bone stock into bone chips as set forth in claim 1, wherein the body further comprises an actuation guide disposed in the channel and the locking element is at least partially disposed in the actuation guide.

10. The milling module for converting bone stock into bone chips as set forth in claim 2, wherein the locking portion comprises a foot that is configured to be received within the locking recess in the lid.

11. The milling module for converting bone stock into bone chips as set forth in claim 10, wherein a force exerted on the control surface removes the foot from the locking recess to allow rotation and removal of the lid from the body.

12. A modular system for converting bone stock into bone chips, the system comprising:

a base module including a motor;

a milling module comprising:

a shell adapted for removeable attachment to the base module, the shell defining an inlet opening through which bone stock is introduced into the shell, the shell further comprising:

a body including a base plate having a top surface, with said base plate defining a control opening and with said body defining a channel extending from said control opening to a lock opening;

a milling element for converting bone stock into bone chips movably disposed in the shell above said base plate and below said inlet opening;

a lid adjacent said lock opening and shaped for removeable attachment to the body to allow removal of residual bone chips from the milling element, wherein said lid defines a locking recess; and a locking element having a control surface and a locking portion, with the control surface at least partially seated in the control opening of the base plate within the channel defined by the body inside the shell, the locking element is movable between:

an unlocked position wherein the locking element is positioned relative to the lid to allow removal of the lid from the body without requiring removal from the base module including the motor; and a locked position wherein the locking element is positioned in said locking recess relative to the lid to prevent removal of the lid from the body;

wherein when the milling module is attached to the base module, the control surface is inaccessible for actuation and the locking element is in the locking position; and wherein when the milling module is not attached to the base module, the control surface is accessible for actuation from an underside of the base plate opposite the top surface.

13. The modular system for converting bone stock into bone chips as set forth in claim 12, wherein the locking element in the locked position prevents rotation of the lid to prevent removal of the lid from the body.

14. The modular system for converting bone stock into bone chips as set forth in claim 12, wherein the locking portion comprises a foot that is configured to be received within the locking recess in the lid.

15. The modular system for converting bone stock into bone chips as set forth in claim 14, wherein a force exerted on the control surface removes the foot from the locking recess to allow the rotation and the removal of the lid from the body.

* * * * *